US005899204A

United States Patent [19]

Cochran

[11] Patent Number: 5,899,204
[45] Date of Patent: * May 4, 1999

[54] DIVE COMPUTER WITH WRIST ACTIVATION

[75] Inventor: Michael J. Cochran, Plano, Tex.

[73] Assignee: Cochran Consulting, Inc., Richardson, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/578,157

[22] Filed: Dec. 29, 1995

Related U.S. Application Data

[63] Continuation-in-part of application No. 08/514,363, Aug. 11, 1995, Pat. No. 5,617,848, which is a continuation of application No. 08/154,022, Nov. 17, 1993, abandoned.

[51] Int. Cl.[6] .......................... A61M 16/00; A62B 9/00; A62B 7/00; G06F 3/00

[52] U.S. Cl. .............................. 128/205.23; 128/202.22; 128/205.22; 128/204.26; 128/201.27

[58] Field of Search ........................ 128/202.22, 204.18, 128/201.27, 204.21–204.23, 204.26, 205.22, 205.23; 310/329, 337; 200/61.45 R, 61.46, 61.45 M, DIG. 2, DIG. 8, DIG. 9, DIG. 20, 404; 362/802; 345/2

[56] References Cited

U.S. PATENT DOCUMENTS

| | | | |
|---|---|---|---|
| 3,556,098 | 1/1971 | Kanwisher et al. | 128/142 |
| 4,192,001 | 3/1980 | Villa | 364/418 |
| 4,563,758 | 1/1986 | Paternostro | 367/132 |
| 4,586,136 | 4/1986 | Lewis | 364/418 |
| 4,658,358 | 4/1987 | Leach et al. | 364/418 |
| 4,757,714 | 7/1988 | Purdy et al. | 73/597 |
| 4,882,678 | 11/1989 | Hollis et al. | 364/413.31 |
| 4,964,404 | 10/1990 | Stone | 128/204.22 |
| 4,970,897 | 11/1990 | Budinger | 73/432.1 |
| 4,999,606 | 3/1991 | Comerford et al. | 340/525 |
| 5,031,160 | 7/1991 | Koizumi et al. | 368/10 |
| 5,033,818 | 7/1991 | Barr | 350/174 |
| 5,103,685 | 4/1992 | Wright | 73/865.1 |
| 5,148,376 | 9/1992 | Sato | 364/558 |
| 5,189,646 | 2/1993 | Sako et al. | 368/10 |
| 5,570,688 | 11/1996 | Cochran et al. | 128/205.23 |

FOREIGN PATENT DOCUMENTS

| | | |
|---|---|---|
| 0182581 | 5/1986 | European Pat. Off. . |
| 0439255 | 8/1994 | European Pat. Off. . |

OTHER PUBLICATIONS

*The International Dictionary of Physics and Electronics*, D. Van Nostrand Co, Inc., copyright 1956, pp. 703–704.

*Primary Examiner*—Kimberly L. Asher
*Attorney, Agent, or Firm*—Gregory M. Howison; Mark W. Handley

[57] ABSTRACT

A wrist unit is provided for allowing the diver to view the breathing parameters that are determined. The breathing parameters are determined by a tank processor via sensors that are disposed on the breathing tank of the diver. These are transmitted to the display unit on the wrist of the diver via a wireless communication link. An inertia switch is provided in the wrist unit, the wrist unit having a watertight housing. The inertia switch is responsive to impacts in the form of tapping on the housing or of rotation of the wrist. When the wrist is rotated, the inertia switch will generate impulses that can be counted and, after a predetermined number, generate a control signal. The control signal controls the on/off function of the wrist unit and also allows switching between alternate displays.

20 Claims, 13 Drawing Sheets

DIVE COMPUTER WITH WRIST ACTIVATION

This Application is a Continuation-in-Part application of U.S. patent application Ser. No. 08/514,363, filed Aug. 11, 1995, now U.S. Pat. No. 5,617,848, which is a Continuation of U.S. patent application Ser. No. 08/154,022, filed Nov. 17, 1993, now abandoned.

BACKGROUND OF THE INVENTION

Although sport diving can be fun, exciting, and physically demanding, there are a variety of potential hazards that must be avoided. In particular, sport diving can be exceedingly dangerous if the diver becomes disoriented or light-headed. Thus, it is desirable for a diver to be able to monitor the rate at which he is consuming air. This task is complicated because the amount of air a diver actually breathes varies with depth even though the diver's breathing rate remains unchanged. For example, if a diver consumes 20 psi per minute while breathing at a normal rate on the surface, he will consume 80 psi per minute if breathing at the same rate at a depth of 99 feet. Thus, for a diver to easily monitor his breathing rate, it is essential that the rate at which he is consuming air be normalized to eliminate the variable of depth.

There are several dive computers available today that display conventional dive parameters such as the amount of air pressure remaining in the user's compressed-air tank, the depth of the user and in some instances the temperature of the surrounding water. Although display of these dive parameters provides the user with a "snap-shot" of his current conditions, they do not allow the user to monitor his rate of air consumption.

Accordingly, an object of the present invention is to provide a dive computer that calculates and displays the user's breathing parameter, which is indicative of the rate at which air pressure in the user's compressed-air tank is decreasing normalized with respect to the depth of the user. Another object of the present invention is to provide a method for calculating the user's breathing parameter.

A diver's breathing parameter is essentially a measure of his breathing efficiency. The more a person dives, the more efficient his breathing should become. Thus, another object of the present invention is to provide a dive computer that stores the diver's breathing parameter in memory for later retrieval so that a diver can track his progress from dive to dive.

Since a diver will not normally stop breathing or suddenly triple his breathing rate, his breathing parameter will not normally go to either an extremely low or high level, and will not normally undergo rapid changes. Thus, a diver's breathing parameter provides an indication of whether the diver is unduly stressed or in trouble and an indication of whether the diver's equipment, including the dive computer itself, is operating correctly. Accordingly, another object of the present invention is to provide a dive computer that provides a visible warning and sounds an audible alarm when the diver's breathing parameter either undergoes a rapid change or reaches an extremely low or high level.

SUMMARY OF THE INVENTION

The present invention disclosed and claimed herein comprises a dive computer for use by a diver having an air tank. The dive computer includes sensors for measuring operating parameters of the tank. A tank processor is provided for processing the sensed operating parameters in accordance with the predetermined processing algorithm to generate processed operating parameters. A transmitter is provided on the tank processor for transmitting the processed operating parameters over a communication link. A wrist processor is operable to be disposed on the wrist of the user to receive from the communication link the processed operating parameters transmitted thereto by the tank processor. The wrist processor has a watertight housing disposed on the wrist with a transparent window disposed therein. A display is mounted in the housing adjacent the window for viewing thereof. A processor section is operable to receive the transmitted operating parameters from the communication link and process the received operating parameters in accordance with a predetermined display processing algorithm to display information on the display. The system is powered by a battery and an inertia switch is provided in the watertight housing for generating a control signal in response to external inertial forces imparted to the housing. The control signal is received by the processing section and, in response thereto, the processor section controls predetermined aspects of the overall operation thereof.

In another aspect of the present invention, the inertia switch is operable to generate the control signal and, in response thereto, the processor section is operable to turn off the display, such that power is not draining from the battery for the display and also to enter a sleep mode. The inertial forces are either impacts at a predetermined frequency and duration or rotation of the wrist. With rotation of the wrist, the diver merely rotates the wrist a predetermined number of times with a predetermined force.

In a further aspect of the present invention, the inertia switch comprises a piezoelectric transducer. The piezoelectric transducer is in the form of a disc shaped member mounted onto a substrate, the substrate in the preferred embodiment also containing the processor section. The mounting of the piezoelectric transducer is achieved with the use of a pedestal that extends upward from the substrate and attached to one edge of the disc shaped piezoelectric member on one side thereof. Electrical contacts on the piezoelectric transducer are utilized for connecting to the processor section, which allows a signal generated by the piezoelectric transducer to be amplified and provide the control signal. The control signal is defined when a predetermined number of impulses in the form of a rotation of the wrist are received by the processor section. By mounting the piezoelectric transducer in a cantilevered configuration, this allows forces other than impacts to the watertight housing to cause stress in the piezoelectric transducer.

In a yet further aspect of the present invention, the processor section is operable to control the display processing operation to operate in accordance with first and second display process algorithms to display first and second display information, respectively. The processor section receives the control signal and, in response thereto, alternates between the first and second displayed information. This allows the user to switch displays.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
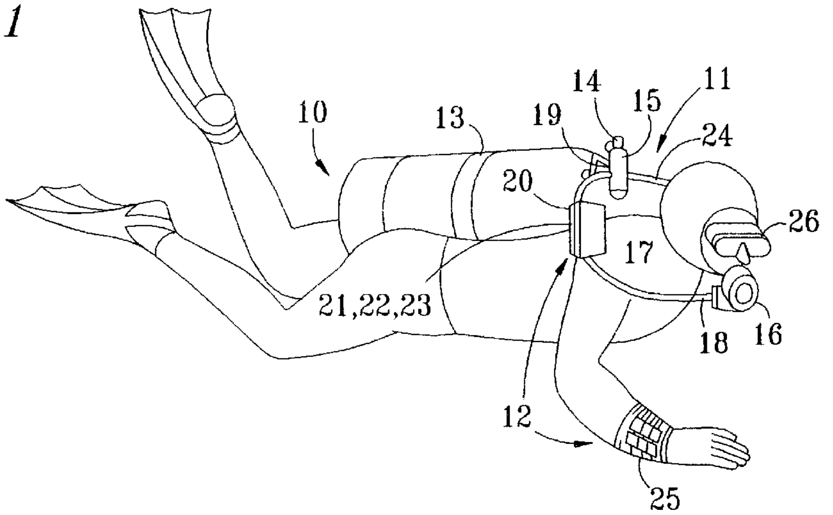
FIG. 1 illustrates a conventional self-contained underwater breathing apparatus (SCUBA), and a dive computer constructed in accordance with the invention.

FIG. 1 illustrates a diver 10 using a conventional self-contained underwater breathing apparatus (SCUBA) 11, and a dive computer 12 constructed in accordance with the present invention.

A conventional self-contained underwater breathing apparatus 11 typically includes a compressed-air tank 13, to which a high pressure tank valve 14 and a first state regulator 15 are connected. A conventional self-contained breathing apparatus also includes a second stage regulator 16 connected to the low pressure port 17 of first stage regulator 15 by a low pressure hose 18. First stage regulator 15 also has a high pressure port 19. The high pressure tank valve 14 has a control knob or handle that allows the controlled release of the air in compressed-air tank 13 by an O-ring sealed high pressure outlet port to first stage regulator 15. First stage regulator 15 has a high pressure inlet port that is typically connected to the high pressure outlet port of valve 14 by a yoke screw. In operation, first stage regulator 15 supplies air from a compressed-air tank 13 to second stage regulator 16 via low pressure hose 18 at a relatively constant, intermediate pressure, substantially independent of the pressure in compressed-air tank 13.

In the preferred form, dive computer 12 consists of a tank unit 20 and a display unit 25. The tank unit connects to the high pressure port 19 of the first stage regulator 15 and may be physically attached by metal clasps 21 through 23 to any available low pressure hose, such as low pressure hose 18 or low pressure hose 24, which goes to the buoyancy compensator. The display unit 25 is adapted to be attached to the user so that it is readily visible. It may be worn by the user like a wristwatch or attached to the user's buoyancy compensator. Alternatively, display unit 25 may be integrated into the user's mask 26 so that dive parameter information can be displayed in the diver's field of view, thus providing a complete "hands free" working environment.

As seen in FIG. 1, in the preferred form the display unit is physically separate from the tank unit. Many of the useful and unique features of dive computer 12 may, however, be incorporated into a dive computer that consists of a single unit.

THE DIVE COMPUTER 12

Figure 2:
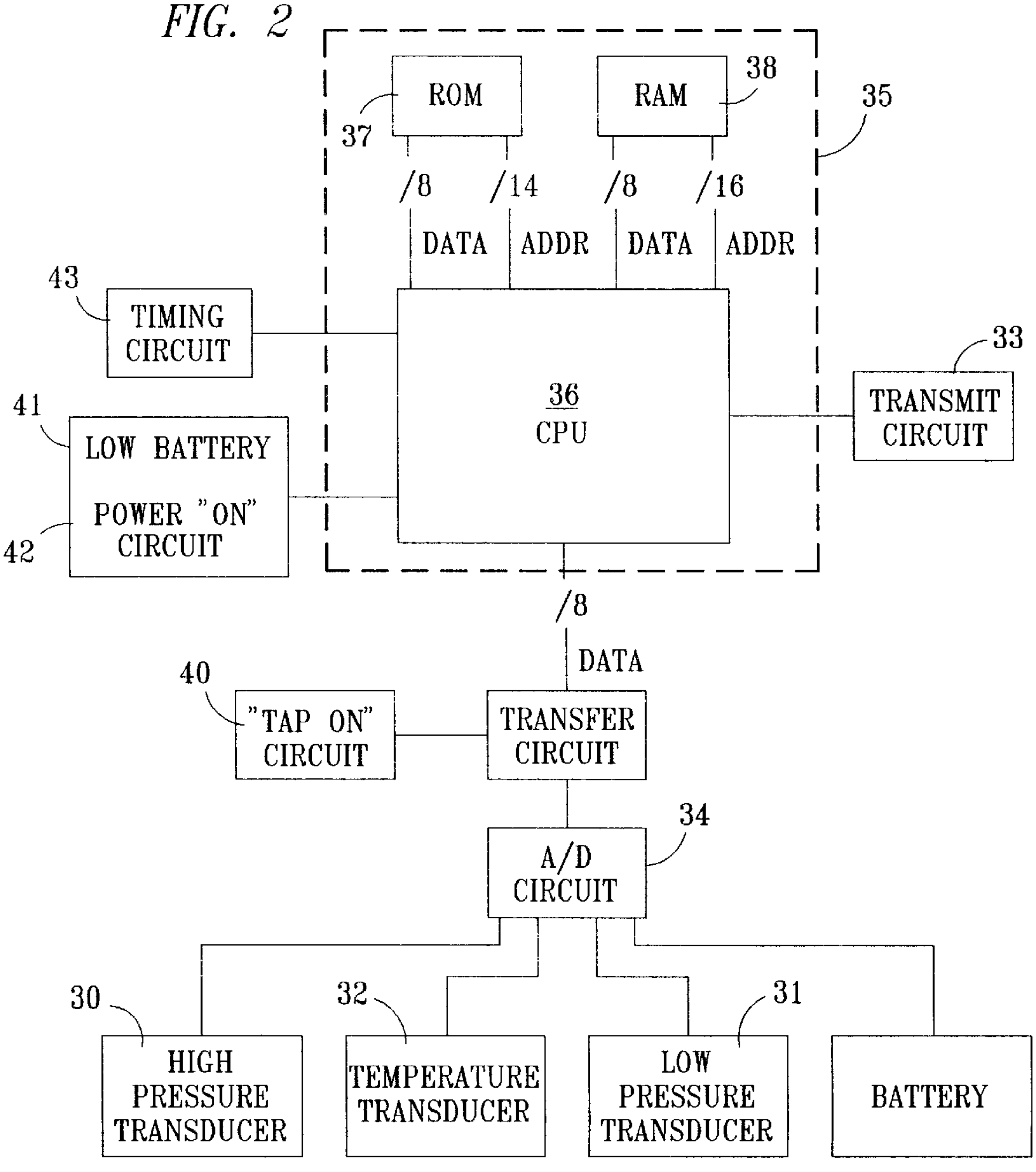
FIG. 2 is a block diagram that illustrates the functional elements of the tank unit of the dive computer.
Figure 4A:
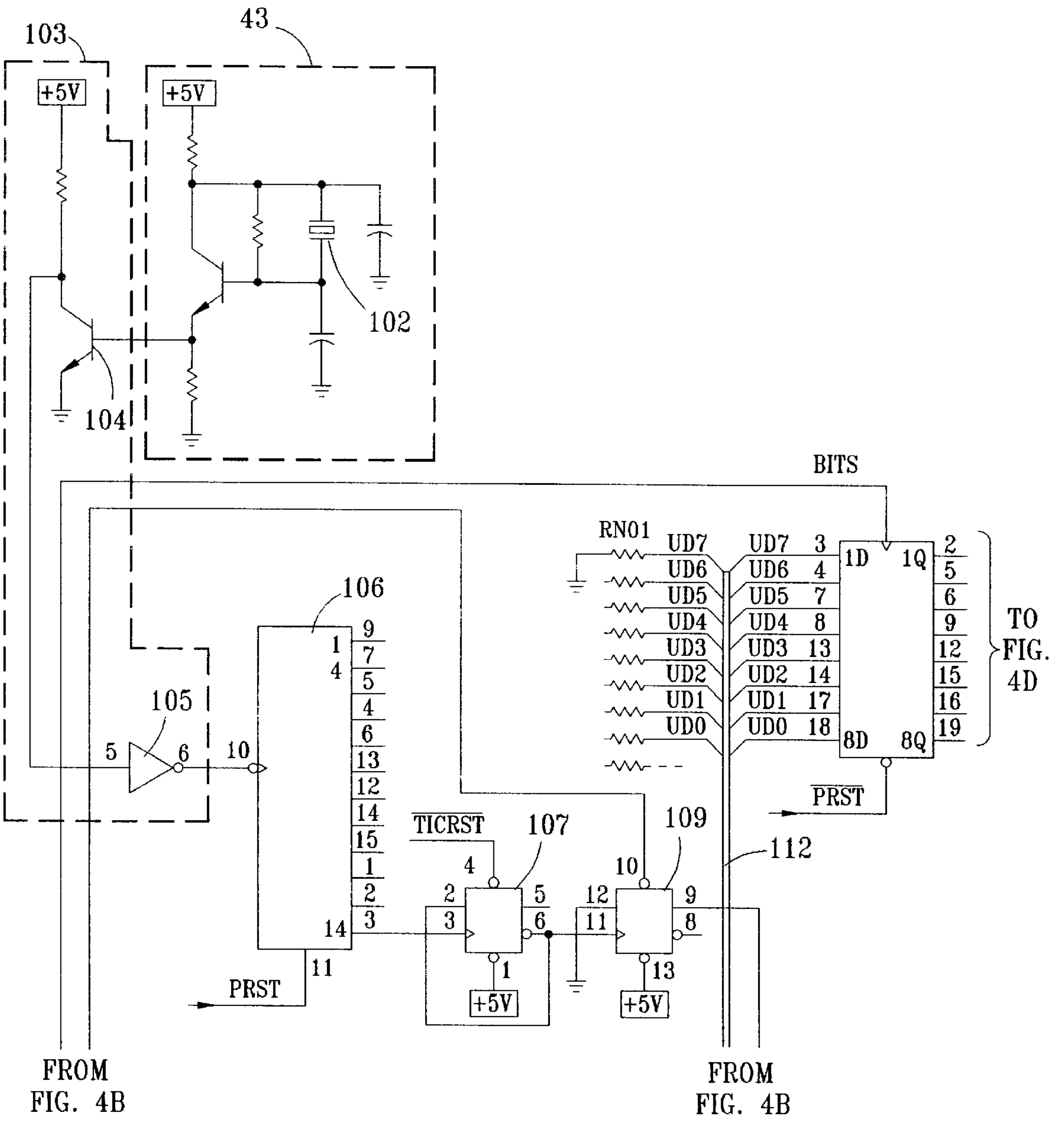
FIGS. 4A through 4F together illustrate an electrical schematic of the tank unit of the dive computer.
Figure 4B:
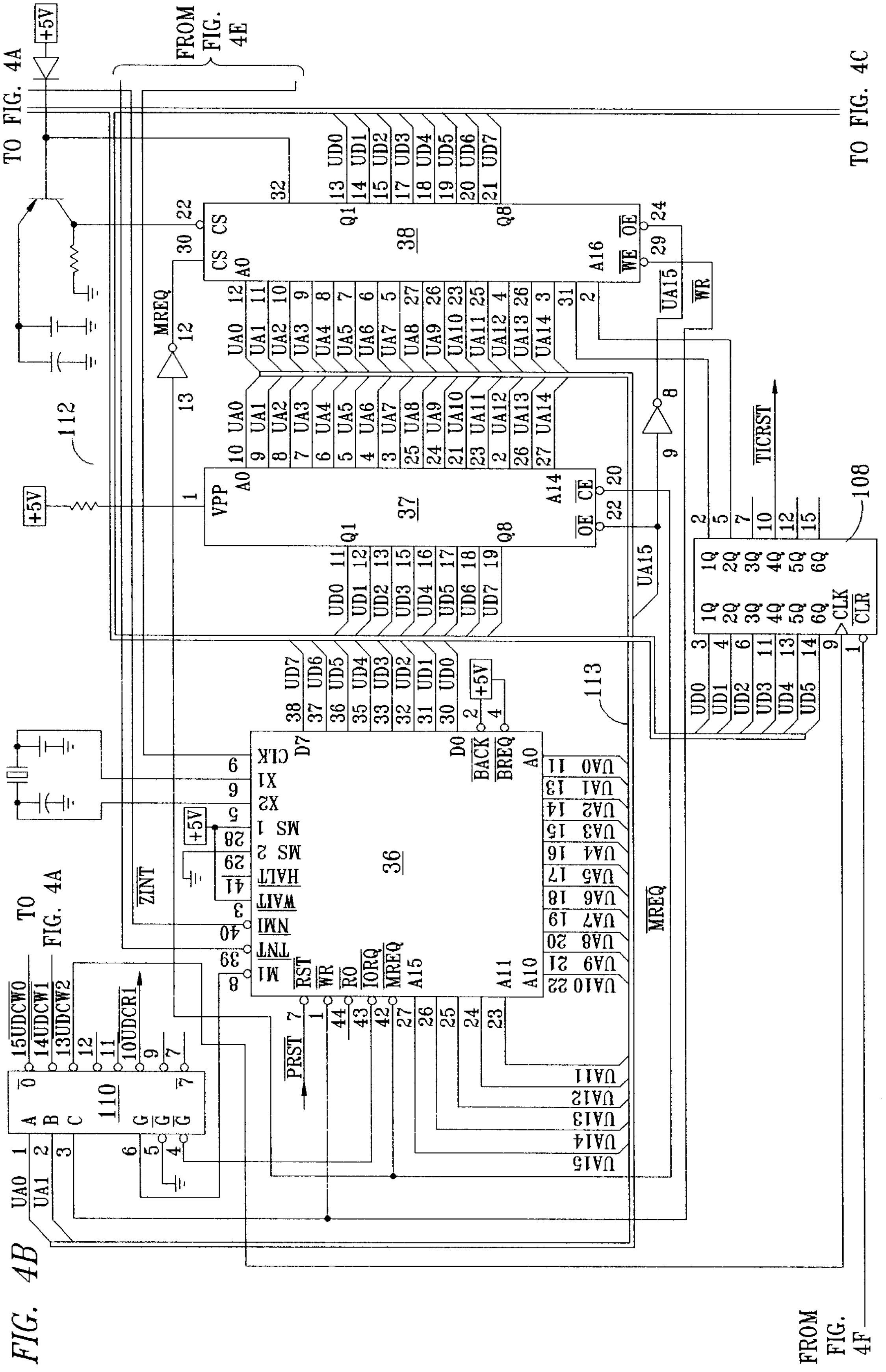
Figure 4C:
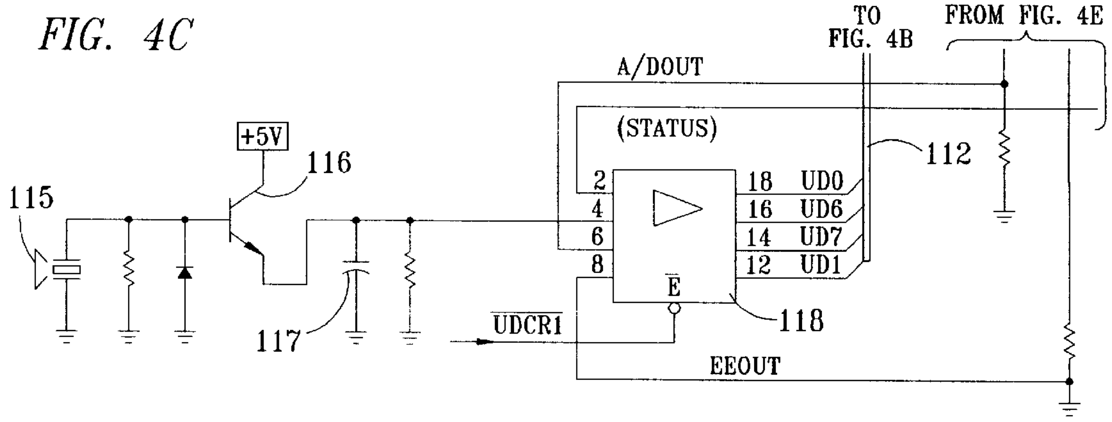
Figure 4D:
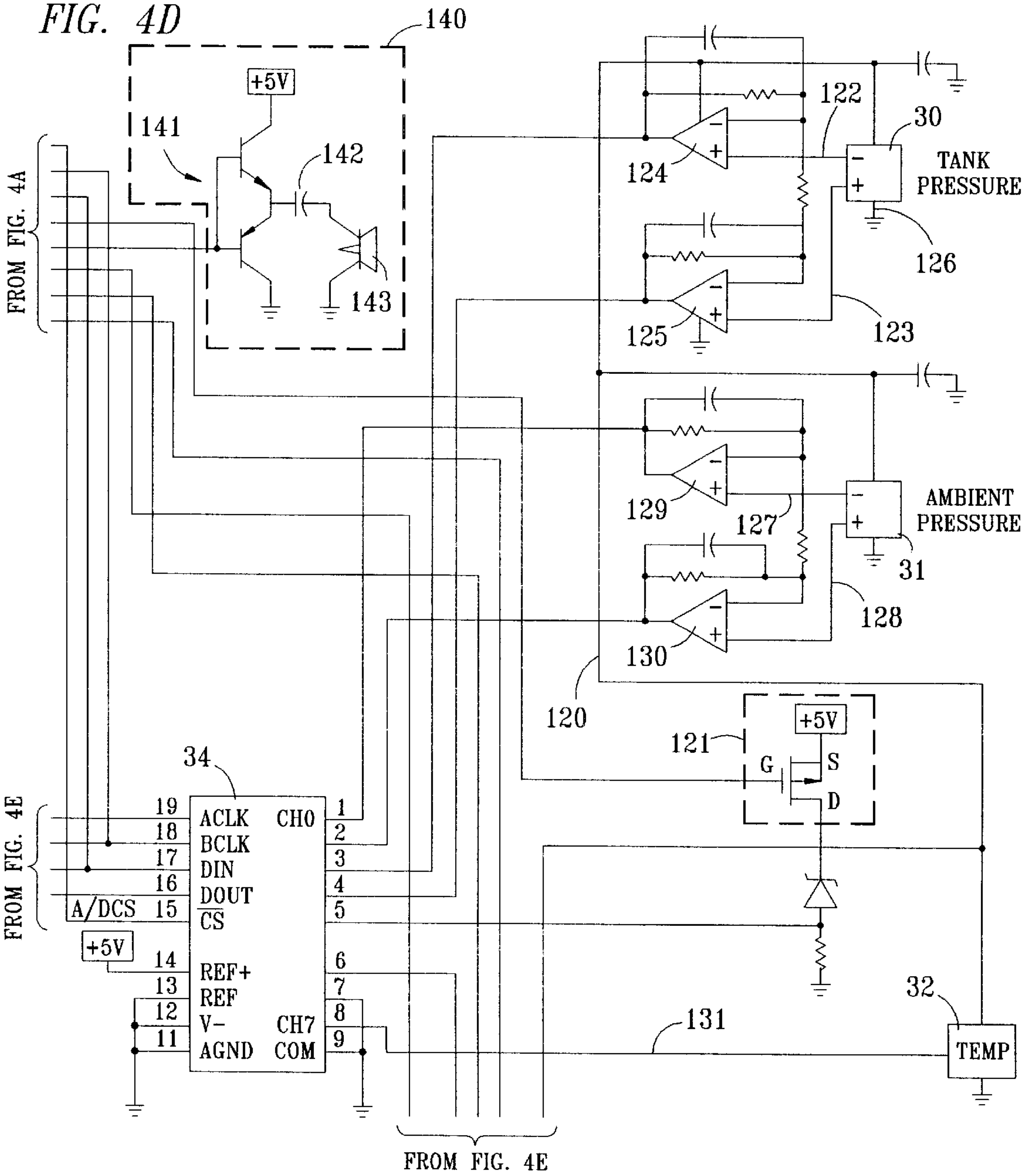
Figure 4E:
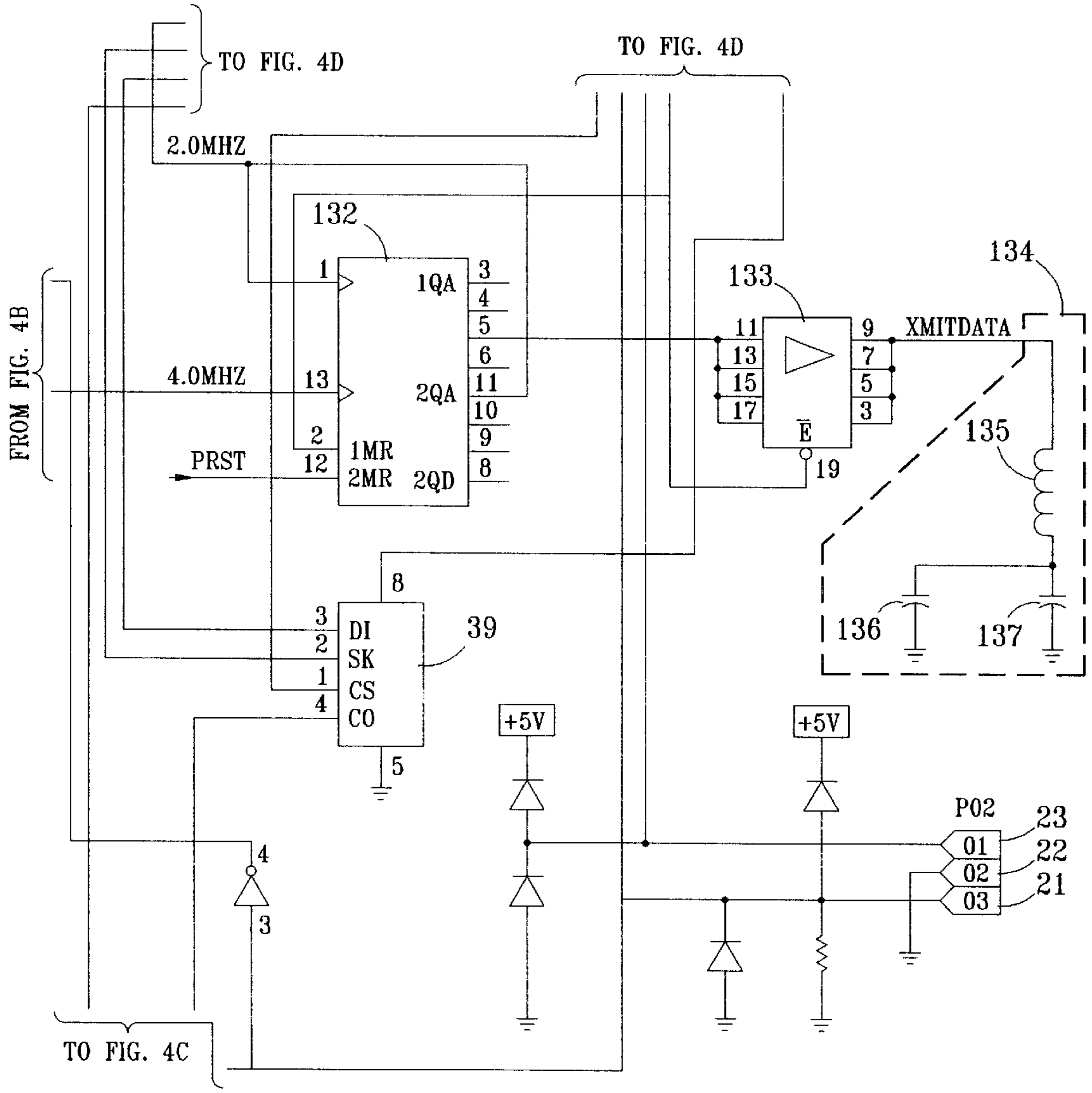
Figure 4F:
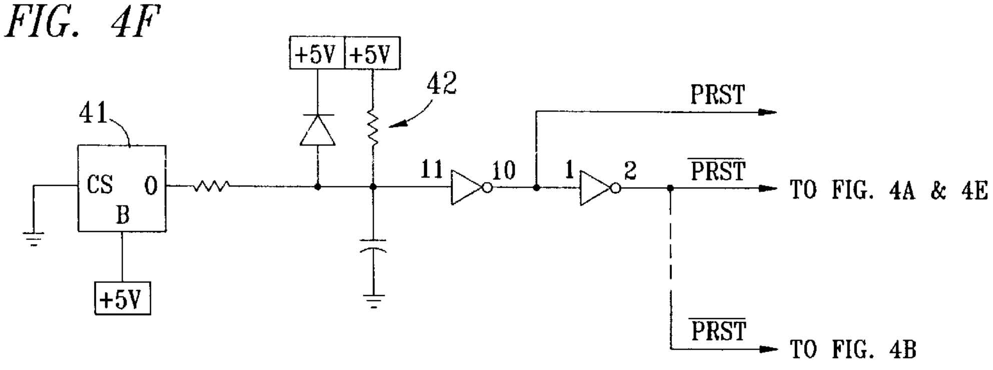
Figure 5A:
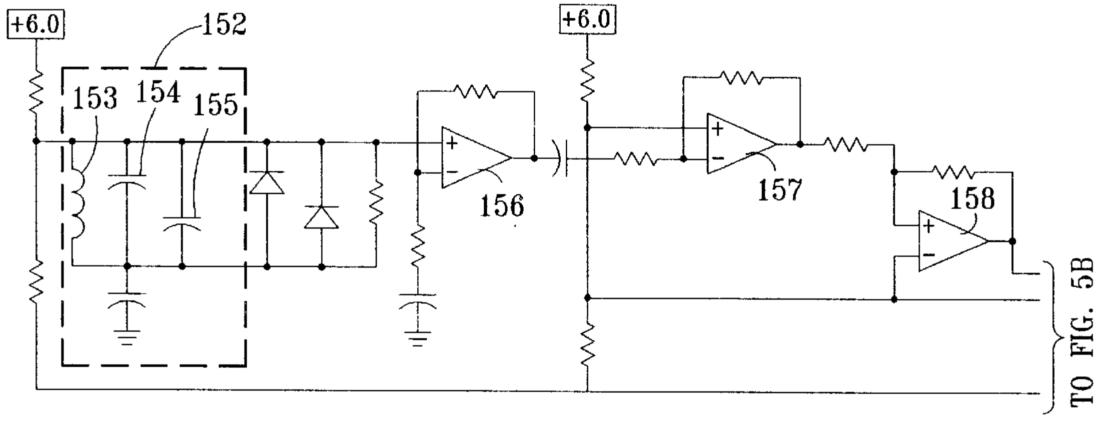
FIGS. 5A through 5D are electrical schematics of the display unit of the dive computer.

FIG. 2 is a block diagram that illustrates the functional elements of the dive computer tank unit 20 shown in FIG. 1. Tank unit 20 includes devices for measuring various dive parameters, including at least a high-pressure transducer 30 for measuring the air pressure in compressed-air tank 13, a low-pressure transducer 31 for measuring ambient pressure, and a temperature sensor 32 for measuring ambient temperature. Tank unit 20 also includes a transmitter 33 for transmitting dive parameter information to display unit 25, so that there is no physical connection between tank unit 20 and display unit 25. In the preferred form, tank unit 20 also includes an A/D converter 34 for converting analog measurements to digital information and a microcomputer 35 to collect, calculate, and store various dive parameters, including the air pressure in compressed-air tank 13, the depth of the user, the length of time the user can safely remain at that depth, and the temperature of the surrounding water. In the preferred form, microcomputer 35 includes a microprocessor 36, a read only memory (ROM) 37, and a random access memory (RAM) 38. Alternatively, microcomputer 35 may include a flash memory device or any other suitable form of memory. Microcomputer 35 may also be consolidated into a single-chip device, such as microcontroller. In the preferred form, tank unit 20 also includes an electrically alterable read only memory (EAROM) 39 (shown in FIG. 4E) for storing the operational parameters of the dive computer; a "tap-on" circuit 40 for turning the tank unit on; a low-battery detect circuit 41 and power-on circuit 42 to ensure proper operation of the tank unit; and a timing circuit 43.

Figure 3:
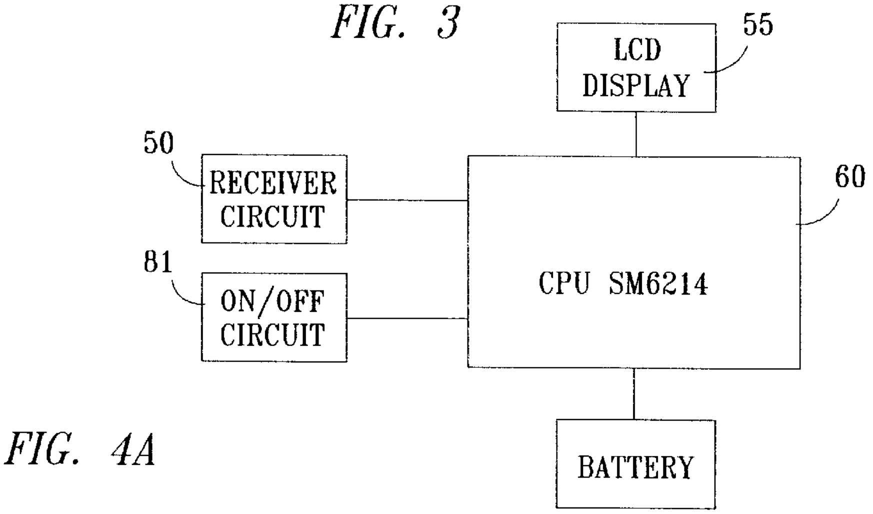
FIG. 3 is a block diagram that illustrates the functional elements of the display unit of the dive computer.

FIG. 3 is a block diagram that illustrates the functional elements of the dive computer display unit 25 shown in FIG. 1. Display unit 25 includes at least a receiver 50 for receiving the signal transmitted by transmitter 33 of tank unit 20 and a liquid crystal display (LCD) 55 for displaying dive parameter information to the user. In the preferred form, the display unit also includes a microcomputer 60 that is used to control operation of the display unit and drive the LCD 55. In the preferred form, microcomputer 60 consists of a microcontroller that is capable of driving LCD 55. Microcomputer 60 may, however, be implemented using a microprocessor with external memory and a separate device capable of driving LCD 55 or a microcontroller and a separate device capable of driving LCD 55. Moreover, many of the functions performed by microcomputer 35 located in tank 20 may be performed by microcomputer 60, in which case microcomputer 35 may be eliminated. A "tap-on" device 81 is also provided that operates in response to a series of sharp impacts, such as a tapping of the fingers on the external housing, to activate certain features, as will be described hereinbelow. This tap-on device will also respond to sharp rotations of the wrist.

Detailed Description of the Tank Unit 20

FIGS. 4A through 4F together illustrate an electrical schematic of the dive computer tank unit 20 shown in FIG. 1. In the preferred form, timing circuit 43 includes a crystal 102 that produces a 32768 Hz signal. This signal is amplified and passed through buffer 103, which consists of transistor 104 and inverter 105, to the input of fourteen-stage divide-by-two counter 106. In the preferred form, counter 106 is 74HC4020 high speed CMOS device available from integrated circuit manufacturers, such as TI and Motorola. The function of counter 106 is to divide the 32768 Hz signal by two fourteen times to generate a 2 Hz signal for input to the clock input of D-type register 107, which functions as a one-stage divide-by-two counter. In the preferred form, D-type register 1067 is a 74HC74, with its Q-output unconnected and its Q_output connected to its D-input. Also, the set pin of register 107 is connected to a +5 volt source and the reset pin is connected to 6-bit latch 108 by control signal TICRST_bar. In the preferred form, 6-bit latch 108 is a 74HC174. The function of control signal TICRST_bar is to suspend normal dive computer operations when the tank unit is attached to a personal computer through a data probe and the dive computer is communicating with the personal computer. (Communication between the dive computer and a personal computer through a data probe is discussed fully below.) During normal operation, the Q_bar-output of register 107 is a 1 Hz signal that is also connected to the clock-input of D-type register 109. In the preferred form, D-type register 109 is also a 74HC74. The D-input of register 109 is connected to ground so that during normal operation the Q-output of register 109 is a one pulse per second signal ZINT_bar. The set pin of register 109 is connected to a +5 volt source and the reset pin is coupled to microprocessor 36 through decoder 110, which is connected to the reset pin of register 109 by control signal UDCW0_bar. The function of control signal UDCW0_bar is to suspend control signal ZINT_bar when the dive computer performs a write operation to I/O address 0.

The ZINT_bar signal connects register 109 to a non-maskable interrupt pin of microprocessor 36. In the preferred form, microprocessor 36 is a Zilog Z84C01, which is a fully static device that draws an extremely low amount of current when not processing data. The function of the ZINT_bar signal is to cause microprocessor 36 to "wake up" and perform its normal dive computer operations. If the tank unit has been turned on when microprocessor 36 receives the ZINT_bar signal, it transmits the user's dive parameters for the previous "awake" period, calculates and stores the user's current dive parameters, and then "goes back to sleep." (The advantage of transmitting the user's previous dive parameters and then calculating and storing the user's current dive parameters is discussed in detail below.) If the tank unit is off when microprocessor 36 receives the ZINT_bar signal, it increments its internal clock, interrogates data bus 112 to determine whether it has been turned off and if it has not been turned on, "goes back to sleep." In either case, during normal operation microprocessor 36 "sleeps" until it again receives a ZINT_bar signal. In the preferred form, it takes a fraction of a second for microprocessor 36 to perform its normal dive computer operations and then go back to sleep. Thus, even when the tank unit is being used during a dive, it is only "awake" and consuming power a fraction of the time, which results in considerable power savings.

Microcomputer 35 Architecture

Microcomputer 35 is connected to data bus 112, which is an 8-bit bus with lines designed UD0 through UD7, and address bus 113, which is a 16-bit bus with lines designated UA0 through UA15. Data bus 112 connects microprocessor 36 to 32K byte read only memory (ROM) 37 and a 128K byte random access memory (RAM) 38. In the preferred form, ROM 37 is a 27C256, which is a 32.768×8-bit electrically programmable read only memory (EPROM) available from Intel, and RAM 38 is a SRM20100, which is a 131,072×8-bit random access memory available from S-MOS. A computer program of conventional form stored in ROM 37 controls operation of microprocessor 36. Lines UA0 through UA14 of address bus 113 connect microprocessor 36 to ROM 37 and RAM 38. Moreover, line UA15 of address bus 113 connects microprocessor 36 to output enable pin (OE_bar) of ROM 37 and, after passing through an inverter, is connected to the output enable pin (OE_bar) of RAM 38 as UA15_bar. Lines UD0 through UD5 also connect microprocessor 36 to 6-bit latch 108 to allow microprocessor 36 to map the 128K bytes of available memory into four 32K byte segments. Through 6-bit latch 108, microprocessor 36 generates address lines A15 and A16, which determine which of the four 32K byte segments of the 128K byte RAM 38 is accessed. The memory request pin (MREQ_bar of microprocessor 36 is connected to ROM 37 through its chip enable pin (CE_bar) and, after passing through an inverter, is connected to RAM 38 through its chip select pin (CS_bar) as MREQ. Also, the write pin (WR_bar) of microprocessor 36 is connected to RAM 38 through its write enable pin (WE_bar). As noted above, a computer program of conventional form is stored in ROM 37. RAM 38 is used to store data.

As noted above, 6-bit latch 108 generates address lines A15 and A16, which determine which of the four 32K byte segments of the 128K byte RAM 38 is accessed. Six-bit latch 108 also generates control signal TICRST_bar, which is used to suspend normal operation of the dive computer when it is communicating to a personal computer through a data probe. Six-bit latch 108 is connected to microprocessor 36 by lines UD0 through UD5 of data bus 112 and through decoder 110 by control signal UDCW2_bar, which is connected to the clock pin of 6-bit latch 108. The function of control signal UDCW2_bar is to cause the data values present on lines UD0 through UD5 of data bus 112 to be latched onto the outputs of 6-bit latch 108.

Data bus 112 also connects microprocessor 36 to 8-bit latch 114, through which microprocessor 36 controls certain operations of the tank unit that will be discussed in detail below. In the preferred form, 8-bit latch 114 is a 74HC273. The clock output of 8-bit latch 114 is coupled to microprocessor 36 through decoder 110, which is connected to 8-bit latch 114 by control signal UDCW1_bar. The function of control signal UDCW1_bar is to cause the data values present on data bus 112 to be latched onto the outputs of 8-bit latch 114.

Decoder 110 is connected to microprocessor 36 by lines UA0 and UA1 of address bus 113 and by liens that connect to pins IORQ_bar, WR_bar, and M1 of microprocessor 36. Through these connections, microprocessor 36 generates three separate write control signals (UDCW0_bar, UDCW1_bar, and UDCW2_bar) and one read control signal (UDCR1_bar, which are the only write and read operations performed by microprocessor 36. In the preferred form, decoder 110 is a 74HC138.

Microprocessor 36 operates at a frequency of 4 MHZ. In the preferred form, the clock generator circuit for microprocessor 36 includes 4 MHZ crystal, which is connected to pins X1 and X2 of microprocessor 36.

The Tank Unit "Tap-On" Circuit 40

In the preferred form, the tank unit includes a "tap-on" switch 40 that allows the user to turn the tank unit on by tapping the area marked on the outside of the case. (The tank unit automatically turns itself off when the nitrogen levels of the twelve tissue compartments approach normal, or after one hour, whichever is longer.) One of the advantages of using a "tap-on" switch 40 is that it eliminates the sealed penetration of the case required for a conventional on-off switch, and thus, minimizes the risk of flooding.

The "tap-on" switch 40 is activated by the user tapping on the area marked on the outside of the tank unit case. Piezoelectric element 115 is mounted to the inside of the tank unit case opposite the marked area for the switch. In the preferred form, piezoelectric current 115 is a device manufactured by Murata Products (Part No. 71313-27-4). When the user taps the marked area, the piezoelectric element 115 senses the vibration and generates a signal that causes transistor 116 to turn on, which in turn charges capacitor 117. Capacitor 117 is connected to an input of gated-buffer 118, which controls of the status of the tank unit 20. In the preferred form, gated-buffer 118 is one-half of a 74HC244, which has four inputs and four outputs. The outputs of gated-buffer 118 are connected to four of the eight data lines that make up data bus 112. These four data lines, UD0, UD1, UD6, and UD7 are the only data lines that can be read by microprocessor 36 and are used to control which operation is performed by the tank unit. The enable pin (E_bar) of gated-buffer 118 is connected to decoder 110 by control line UDCR1_bar. The function of UDCR1_bar is to cause gated-buffer 118 to transfer the data values present at the inputs to the outputs so that they can be read by microprocessor 36. When capacitor 117 is charged, activation of control line UDCR1_bar causes gated-buffer 118 to set a positive signal on data bus 112 line UD6.

As noted above, if the tank is off when it receives control signal ZINT_bar, microprocessor 36 increments its internal clock and then interrogates data bus 112 to determine whether it has been turned off. If the user has tapped the area marked on the outside of the case during the previous second, the charge on capacitor 117 is transferred by gated-buffer 118 to data line UD6, which is read by microprocessor 36 to an internal register. Once the data has been read into an internal register, microprocessor 36 performs a test-bit operation to determine whether the tank unit has been turned on. When microprocessor 36 determines that the tank unit has been turned on, it begins its normal dive computer operations. (If the tank unit has been turned on and senses that ambient pressure corresponds to sea level or zero depth, the unit defaults to surface mode.) After the tank unit is turned on, it begins transmitting the user's dive parameters to the display unit and calculating and storing the user's current dive parameters each time it receives a ZINT_bar signal from register 109.

Dive Parameters

In the preferred form, the tank unit includes at least means for measuring the air-pressure in the user's compressed-air tank 13, ambient pressure, and ambient temperature.

The pressure in the user's compressed-air tank 13 is measured by transducer 30, which in the preferred form is located outside the case of the tank unit in the connector that connects the tank unit to high pressure port 19 of first stage regulator 15. In the preferred form, transducer 30 is a high-pressure transducer available from Luca Nova Sensors (Part No. NPI-15X-C00XXX), which is capable of providing a linear measurement of pressure from zero to 4000 psi. (The threads of transducer 30 are modified to match a standard first stage regulator connection.) Four wires connect transducer 30 to the interior of the tank unit. One wire 120 connects transducer 30 to a +5 volt source through p-channel power MOSFET 121. Two more wires, 122 and 123, connect the differential outputs of transducer 30 to the positive inputs of operational amplifiers (op-amps) 124 and 125, respectively. In the preferred form, op-amps 124 and 125 are both LPC660s, available from National Semiconductor. The fourth wire 126 connects transducer 30 to ground. Op-amps 124 and 125 are connected in the conventional fashion to amplify the differential outputs of transducer 30. The outputs of op-amps 124 and 125 are connected to A/D converter 34.

Ambient pressure is measured by transducer 31, which is mounted on the inside of the tank unit case and is electrically connected in the same manner as transducer 30. In the preferred form, transducer 31 is a low-pressure transducer available from Sen-Sym (Part No. SX100A), which is capable of providing a linear measurement of pressure from zero to 100 psi. Four wires connect to transducer 31. Wire 120, which connects transducer 30 to a +5 volt source through p-channel power MOSFET 121, also connects transducer 31 to that +5 volt source through MOSFET 121. Two more wires, 127 and 128, connect the differential outputs of transducer 31 to the positive inputs of op-amps 129 and 130, respectively. In the preferred form, op-amps 129 and 130 are both LPC660s. The fourth wire connects transducer 31 to ground. Op-amps 129 and 130 are connected in the conventional fashion to amplify the differential outputs of transducer 31. The outputs of op-amps 129 and 130 are connected to A/D converter 34.

Ambient temperature is measured by temperature sensor 32, which is physically attached to one of the low pressure hose clasps. In the preferred form, temperature sensor 32 is a LM34DZ available from National Semiconductor. Three wires connect to temperature sensor 32. Wire 120, which connects transducers 30 and 31 to a +5 volt source through p-channel power MOSFET 121, also connects to temperature sensor 32. A second wire attaches temperature sensor 32 to ground and the third wire 131 connects the output of the temperature sensor 32 to A/D converter 34.

P-channel power MOSFET 121 is coupled to microprocessor 36 through 8-bit latch 114, which is connected to microprocessor 36 by data bus 112. Specifically, the input to 8-bit latch 114 on line UD4 controls whether MOSFET 121 is turned on. MOSFET 121 is only turned on to measure the user's dive environment, which minimizes the power used by the tank unit and maximizes the battery life of the tank unit.

In the preferred form, A/D converter 34 is a LTC1290, which is a serial device available from Linear Technologies Corporation. A/D converter 34 receives analog dive parameter measurements from high-pressure transducer 30, ambient-pressure transducer 31, and temperature sensor 32, converts those measurements to digital data and transmits that data to microprocessor 36 through gated-buffer 118. The serial output pin (DOUT) of A/D converter 34 is connected to the input of gated-buffer 118, which transfers that data onto line UD7 when control line $\text{UDCR1}_{13}$ bar is activated by microprocessor 36. Serial data is shifted out of A/D converter 34 and through gated-buffer 118 in accordance with the shift clock (SCLK) signal, which is generated by microprocessor 36 through 8-bit latch 114.

A/D converter 34 is a successive approximation-type device, which requires a clock input (ACLK). The clock input of A/D converter 34 is provided by microprocessor 36 through divider 132. One of the functions of divider 132 is to receive a 4 MHZ signal from microprocessor 36 and divide it by two to generate a 2 MHZ signal for A/D converter 34. (Divider 132 also takes this same 2 MHZ signal and divides it by eight to generate a 250 Khz signal that is used by the tank unit to transmit to the display unit 25.)

A/D converter 34 is also coupled to microprocessor 36 through 8-bit latch 114 by the data-in pin (DIN) and the chip-select pin (CS_bar). The DIN connection allows microprocessor 36 to write data to A/D converter 34 and the chip-select connection allows microprocessor 36 to choose between A/D converter 34 and electrically alterable read only memory (EAROM) 39, which shares the data in and shift clock connections of A/D converter 34.

Breathing Parameter Calculations

In addition to monitoring the user's conventional dive parameters, such as the depth of the user, the air pressure in compressed-air tank 13, and the length of time that the user can safely remain at that depth, microcomputer 35 also computes the user's breathing parameter, which is the rate at which the air pressure in compressed-air tank 13 is decreasing normalized for depth. For example, if the user is on the surface and is breathing such that air pressure in compressed-air tank 13 is decreasing at a rate of 20 psi per minute, then the user's breathing parameter will be 20. If the user is at a depth of 66 feet and is breathing at the same rate, such that the air pressure in compressed-air tank 13 is decreasing at a ate of 60 psi per minute, the user's breathing parameter will still be 20. By eliminating the variable of depth, the user can monitor his actual rate of air consumption.

Figure 6:
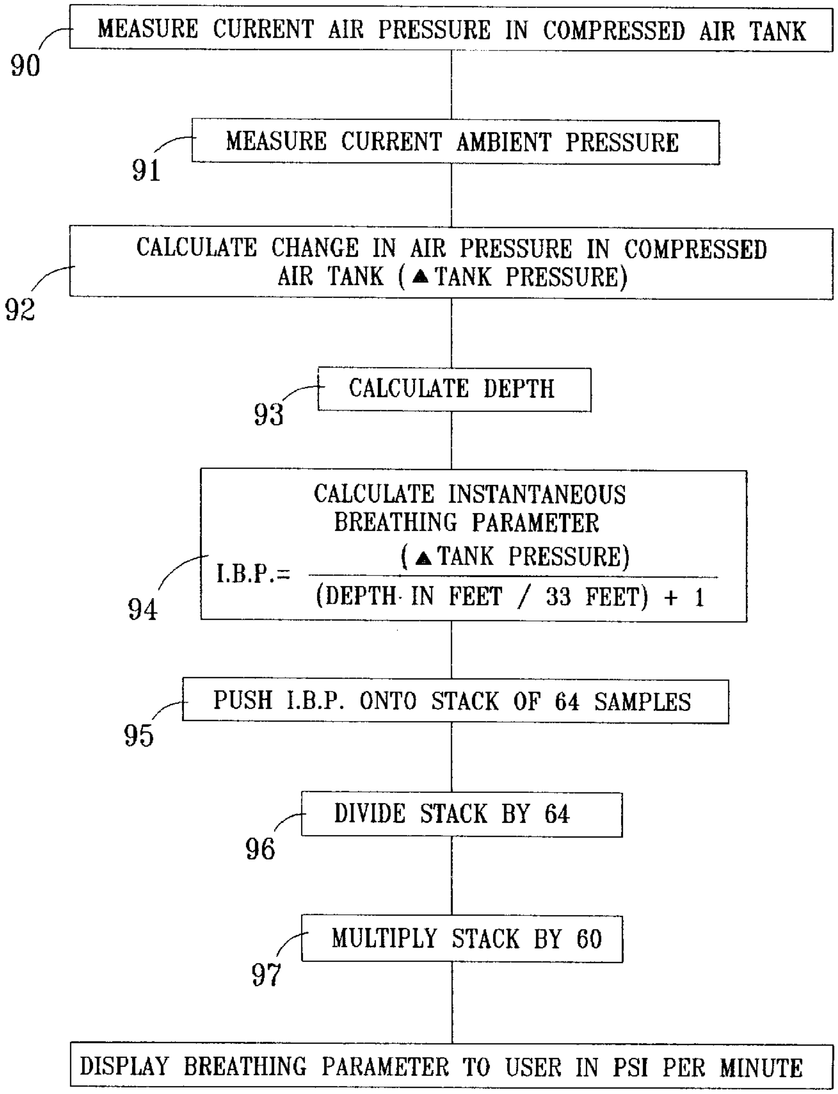
FIG. 6 is a flow chart that illustrates the preferred method of calculating the user's breathing parameter.

FIG. 6 is a flow chart that illustrates the preferred method of calculating the user's breathing parameter. In the preferred form, high-pressure transducer 30 periodically measures the air pressure in compressed-air tank 13 and generates an analog signal that is converted by A/D converter 34 into a digital signal for use by microcomputer 35. (Block 90). During the same time period, low-pressure transducer 31 measures ambient pressure and generates an analog signal, which is also coupled to microcomputer 35 through A/D converter 34. (Block 91). Microcomputer 35 calculates the change in air pressure in compressed-air tank 13 (Δ tank pressure) by subtracting the air pressure reading of the previous time period from the air pressure reading of the current time period. (Block 92). Microcomputer 35 also calculates the user's current depth based on the ambient pressure reading measured by transducer 35. (Block 93). With this information, microcomputer 35 calculates the user's instantaneous breathing parameter, which is equal to the change in tank pressure normalized for depth. (Block 94):

$$I.B.P. = \frac{\Delta \text{ tank pressure}}{\frac{\text{depth in feet}}{33 \text{ feet}} + 1}$$

Microcomputer 35 calculates the user's breathing parameter by averaging the user's current instantaneous breathing parameter with the user's previous sixty-three (63) instantaneous breathing parameters, which are stored in memory. (Blocks 95 and 96). Averaging the user's instantaneous breathing parameter over a 64 second period eliminates rapid variations that may occur in the user's instantaneous breathing parameter. The user's average breathing parameter is then multiplied by 60 so that the actual breathing parameter displayed to the user is indicative of the rate at which the pressure in compressed-air tank 13 is decreasing in psi per minute normalized for depth. (Block 97).

Alternatively, the user's breathing parameter can be calculated by summing the user's current instantaneous breathing parameter with the user's previous 59 instantaneous breathing parameters, which are stored in memory. This method eliminates the need to divide by 64 and multiply by 60, and still results in breathing parameters being displayed to the user, which is indicative of the normalized rate at which the pressure in compressed-air tank 13 is decreasing in psi per minute.

Operational Parameters

The operational parameters of the dive computer 12 are stored in the tank unit in EAROM 39. In the preferred form, EAROM 39 is a NMC93C66, which is a 4096 bit EAROM available from National Semiconductor. EAROM 39 is coupled to microprocessor 36 through 8-bit latch 114. As noted above, EAROM 39 shares its data in (DIN) and shift clock (SCLK) connections to microprocessor 36 with A/D converter 34. EAROM 39 is also coupled to microprocessor 36 through 8-bit latch 114 by a chip select pin (CS_bar), which allows microprocessor 36 to choose between EAROM 39 and A/D converter 34. EAROM 39 is also coupled to microprocessor 36 through gated-buffer 118. The Data Out pin (DO) of EAROM 39 is connected to the input of gated-buffer 118, which transfers data transmitted from EAROM 39 onto data bus 112 when control line UDCR1_bar is activated by microprocessor 36. Serial data is shifted out of EAROM 39 and through gated-buffer 118 in accordance with the shift clock (SCLK) signal, which, as noted above, is generated by microprocessor 36 through 8-bit latch 114.

In the preferred form, the user can customize the operational parameters of dive computer 12 by setting various control bits that control execution of the dive computer control program stored in ROM 37. (The user accesses EAROM 39 by connecting the tank unit 20 to a personal computer 200 through data probe 150. Data probe 150 and the connection of the dive computer tank 20 to a personal computer 200 through data probe 150 are discussed in detail below.) By setting various control bits in EAROM 39, the user can select whether information is displayed in English or metric units, and if the user chooses to display information in metric units, the user can further select whether pressure is displayed in bars or kg/cm$^2$. In the preferred form, the user can also select the rate at which dive parameter information is stored by the dive computer tank unit 20 and the length of time the display unit 25 displays information in alternate modes of operation. Moreover, the user can control the method used by the dive computer to model nitrogen compartments and select whether the dive computer modifies the method its uses to model nitrogen compartments depending on other variables, such as the ambient temperature of the water or changes in the user's breathing parameter. The user can also control whether the dive computer sounds an audible alarm and the circumstances under which the dive computer sounds an audible alarm.

In the preferred form, each dive computer has an identification number stored in EAROM in both the tank unit 20 and the display unit 25. This identification number is used the ensure the integrity of the communication link between the tank unit and the display unit. The dive computer identification number stored in EAROM 39 is included in each transmission from the tank unit 20 to the display unit 25. The same dive computer identification number is also stored in EAROM in the display unit 25. When the display unit 25 receives a transmission from the tank unit 20, it first compares the identification number transmitted with the signal to determine if it originated at its tank unit 20. If the identification number transmitted by the tank unit 20 matches the identification number of the display unit 25, the display unit 25 displays the information contained in that transmission. If, however, the identification numbers do not match, the display unit 25 discards the transmitted information. Thus, if the display unit 25 receives a signal from a nearby tank unit that is not the user's, it will not mislead the user by displaying the information contained in that signal. In the preferred form, the user can change the identification number transmitted by the tank unit by accessing EAROM 39 through data probe 150, so that a single tank unit can be used with other display units or display devices.

Power for EAROM 39 is supplied through P-channel power MOSFET 121, which minimizes the power used by EAROM 39 and helps to maximize the battery life of the tank unit.

The Tank Unit Data Probe Connection

As noted above, the tank unit includes three metal clasps 21 through 23 that may be used during a dive to connect the tank unit 20 to the user's low-pressure hose 24. These three metal clasps 21 through 23 can also be used to connect the dive computer to a personal computer 200 through the data probe 150. As noted above, the user can then select the operational parameters of the dive computer 12. This connection can also be used to download stored information from the tank unit 20 to a personal computer 200.

Metal clasp 21 is used to transmit serial data from personal computer 200 to the tank unit 20. It is connected to data bus 112 through gated-buffer 118. As noted above, microprocessor 36 transmits control signal UDCD1_bar to transfer the data at the inputs of gated-buffer 118 onto data bus 112, where it can be read. Thus, microprocessor 36 can serially read data from metal clasp 21 through gated-buffer 118. Metal clasp 23, which is connected to microprocessor 36 through 8-bit latch 114, is used to transmit serial data from the tank unit to the personal computer. Metal clasp 22 is electrically connected to ground.

Figure 10:
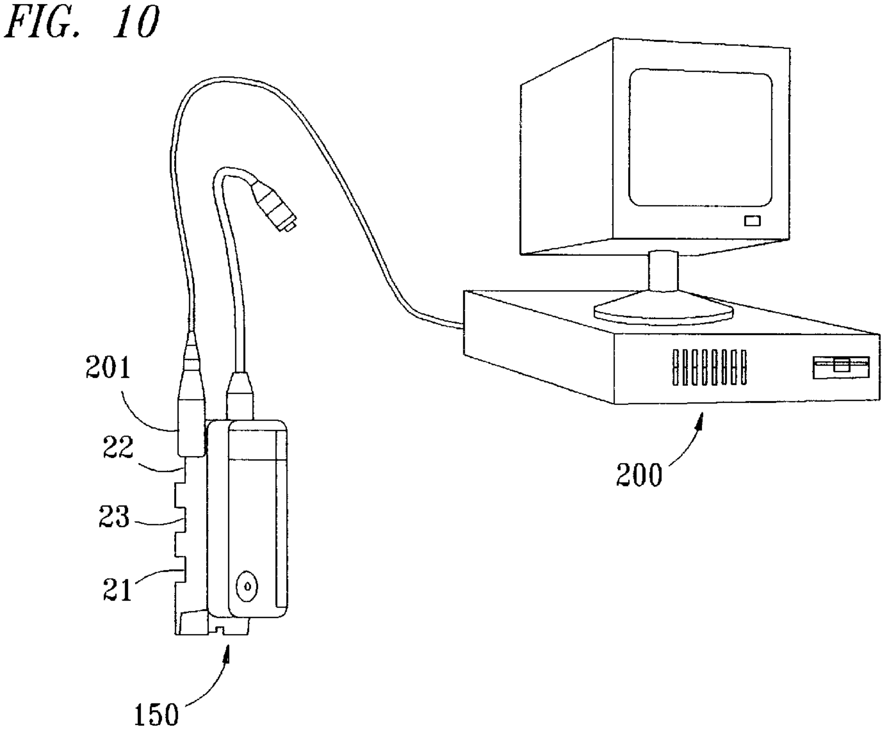
FIG. 10 illustrates a personal computer, connected to the dive computer, shown in FIG. 1 through a data probe.
Figure 11:
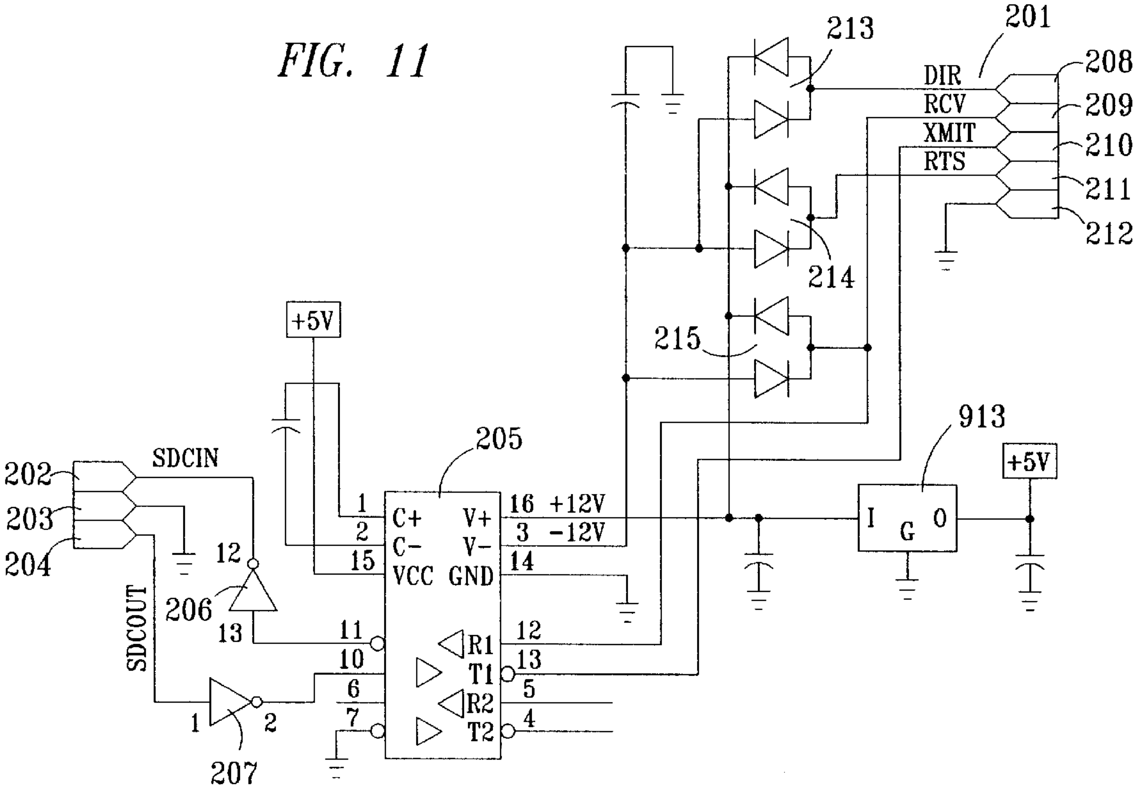
FIG. 11 is an electrical schematic of the data probe illustrated in FIG. 10.

The data probe 150 used to connect the tank unit 20 to personal computer 200 is illustrated in FIGS. 10 and 11.

Tank Unit Transmitter Circuit 33

As noted above, divider 132 receives a 4 MHZ signal from microprocessor 36, which it first divides by two and then divides by eight to generate a 250 Khz signal that is used to transmit data to the display unit. The 250 Khz signal generated by divider 132 is connected by buffer/driver 133. In the preferred form, buffer/driver 133 is one-half of a 74HC244. Microprocessor 36 is also coupled to the enable pin (E_bar) of buffer/driver 133 through 8-bit latch 114. This connection between microprocessor 36 and buffer/driver 133 is used by microprocessor 36 to modulate the 250 Khz signal with dive parameter data to be transmitted to the display unit. In the preferred form, a pulse code modulation technique is used to modulate the 250 Khz signal received by buffer/driver 133. The signal generated by buffer/driver 133 is connected to the tank unit antenna 134. In the preferred form, tank unit antenna 134 consists of inductor 135, which is made up of a ferrite core wrapped by approximately 60 turns of a #30 gauge copper wire, connected in series with two capacitors, 136 and 137, which are also connected in parallel to ground. Capacitors 136 and 137 are tuned to impedance match the antenna at the desired transmission frequency. Antenna 134 generates a modulated magnetic field that inductively couples inductor 135 in the tank unit transmitter circuit to an inductor located in receiver circuit 50 contained in the display unit 25.

Tank Unit Alarm Circuit 140

The tank unit alarm circuit 140 includes buffer 141, which consists of two transistors, capacitor 142, and speaker 143. In the preferred form, speaker 143 is a standard 8 ohm speaker available from Shogyo International (Part No. CP-28CT). Tank unit alarm circuit 140 is coupled to microprocessor 36 through 8-bit latch 114. The tone generated by speaker 143 corresponds to the frequency at which microprocessor 36 alternates the bit coupled to buffer 141. In the preferred form, microprocessor 36 sweeps the rate at which it alternates the bit coupled to buffer 141 from a low audible frequency to a high audible frequency over a one-half second period, once every second for five seconds. Thus, the warning signal generated by the tank unit is a one-half second sweep by speaker 143 from a low tone to a high tone, once every second for five seconds.

In the preferred form, the tank unit alarm circuit sounds an audible alarm whenever certain dive parameters, such as the amount of air left in the user's compressed-air tank, reach dangerous levels. Specifically, the tank unit alarm circuit sounds an audible alarm if the diver's breathing parameter suddenly undergoes a rapid change or reaches an extremely high or low level. In the preferred form, the user can select which dive parameters cause an audible alarm to sound and set the dive parameter levels at which the audible alarm sounds by setting various control bits in EAROM 39.

Low Battery Detect 41 and Power-Up Reset Circuit 42

The tank unit includes a low battery detect 41 and power-up reset circuit 42 to ensure proper operation of the dive computer. In the preferred form, low battery detect circuit 42 consists of a SCI17701J available from S-MOS, which transmits a signal that holds microprocessor 36 at reset whenever the batteries in the tank unit are low. The power-up reset circuit 42 includes a diode and resistor connected in parallel to a +5 volt source and through a capacitor to ground. When the user changes the batteries in the tank unit, this circuit causes a reset signal to be sent to microprocessor 36. Whenever microprocessor 36 receives a reset signal, it automatically runs a self-test diagnostic program to ensure that the tank unit is functioning properly.

Automatic Depth Calibration

The same three metal clasps 21 through 23 that are used to connect the tank unit to the user's low-pressure hose 24 during a dive and to data probe 150 are also used to calibrate the dive computer's depth measurements for fresh water and sea water. When the tank unit detects that it has been submerged, microprocessor 36 transmits at +5 volt pulse into the surrounding water through metal clasp 23 and measures the voltage signal detected at metal clasp 21. In addition to being coupled to microprocessor 36 through gate-buffer 118, metal clasp 21 is also coupled to microprocessor 36 through A/D converter 34. Since sea water is a better conductor than fresh water, the tank unit can determine the salinity of the water into which it has been submerged by the strength of the signal received at metal clasp 21. After microprocessor 36 determines whether the user is in sea water or fresh water, it stores that information and calibrates its depth measurements accordingly. In the preferred form, the calibration process takes place only after tank unit 20 has been submerged to a depth of approximately 5 feet. This process is repeated, however, each time the tank unit 20 is submerged.

Detailed Description of the Display Unit 25

FIGS. 5A through 5D together illustrate is an electrical schematic of the display unit 25 of the dive computer shown in FIG. 1. Operation of the display unit is controlled by microcomputer 60, which is a 4-bit microcontroller capable of driving a liquid crystal display 55. In the preferred form, microcomputer 60 is an S-MOS SMC6214. As noted above, microcomputer 60 is a single chip device that includes a 4096×12-bit ROM and a 208×4 RAM. The ROM of microcomputer 6770 contains a computer program of conventional form that controls operation of microcomputer 60. Also, as noted above, the display unit includes EAROM 151, which contains the identification number of the display unit 25. EAROM 151 is directly connected to microcomputer 60. In the preferred form, the EAROM 151 is an NMC93C06, which is a 256-bit EAROM available from National Semiconductor.

The Display Unit Receiver Circuit 50

The display unit includes an antenna 152 that receives the modulated magnetic field generated by the tank unit antenna 37. In the preferred form, the display unit antenna 152 consists of inductor 153, which is formed by a ferrite core wrapped by approximately 100 turns of a #30 gauge copper wire, connected in parallel with two capacitors, 154 and 155, which are also connected in parallel. Capacitors 154 and 155 are tuned to impedance match the display unit antenna 152 at the desired transmission frequency. As noted above, the preferred information is transmitted from the tank unit to the display unit by a 250 Khz modulated magnetic field. Specifically, the magnetic field generated by the tank unit antenna induces a magnetic flux through the ferrite core of inductor 153, which in turn causes a current to be generated in the winding of inductor 153. The signal received by display unit antenna 152 is limited by back-to-back diodes to attenuate strong magnetic coupling between the tank unit 20 and the display unit 25 and coupled through a series of four op-amps 156 through 159, which translate the signal received by the display unit into a modulated 250 Khz square wave. In the preferred form, each of the four op-amps is a TL064 available from either TI or Motorola.

The dive parameter data contained in the modulated signal received by the tank unit is extracted by demodulator 160. In the preferred form, demodulator 160 is a simple circuit that consists of capacitor 161 connected in series to diode 162, which is connected to ground, and through diode 163 to a resistor 164 and capacitor 165, which are connected in parallel to ground, and the gate of transistor 166. The source of transistor 166 is connected through a resistor to a +3.5 volt source and to an input to microcomputer 60 through data line RDATA_bar. The emitter of transistor 166 is connected to ground. The presence of a pulse on the output of op-amp 159 causes capacitor 165 to charge up and transistor 166 to turn on, which in turn causes data line RDATA_bar to be pulled to ground. The absence of a pulse on the output of op-amp 159 causes capacitor 165 to discharge to ground through resistor 164, which turns off transistor 166 and causes data line RDATA-bar to float high. In this fashion, the display unit microcomputer 60 receives the digital information transmitted by the tank unit microcomputer 36.

Figure 5B:
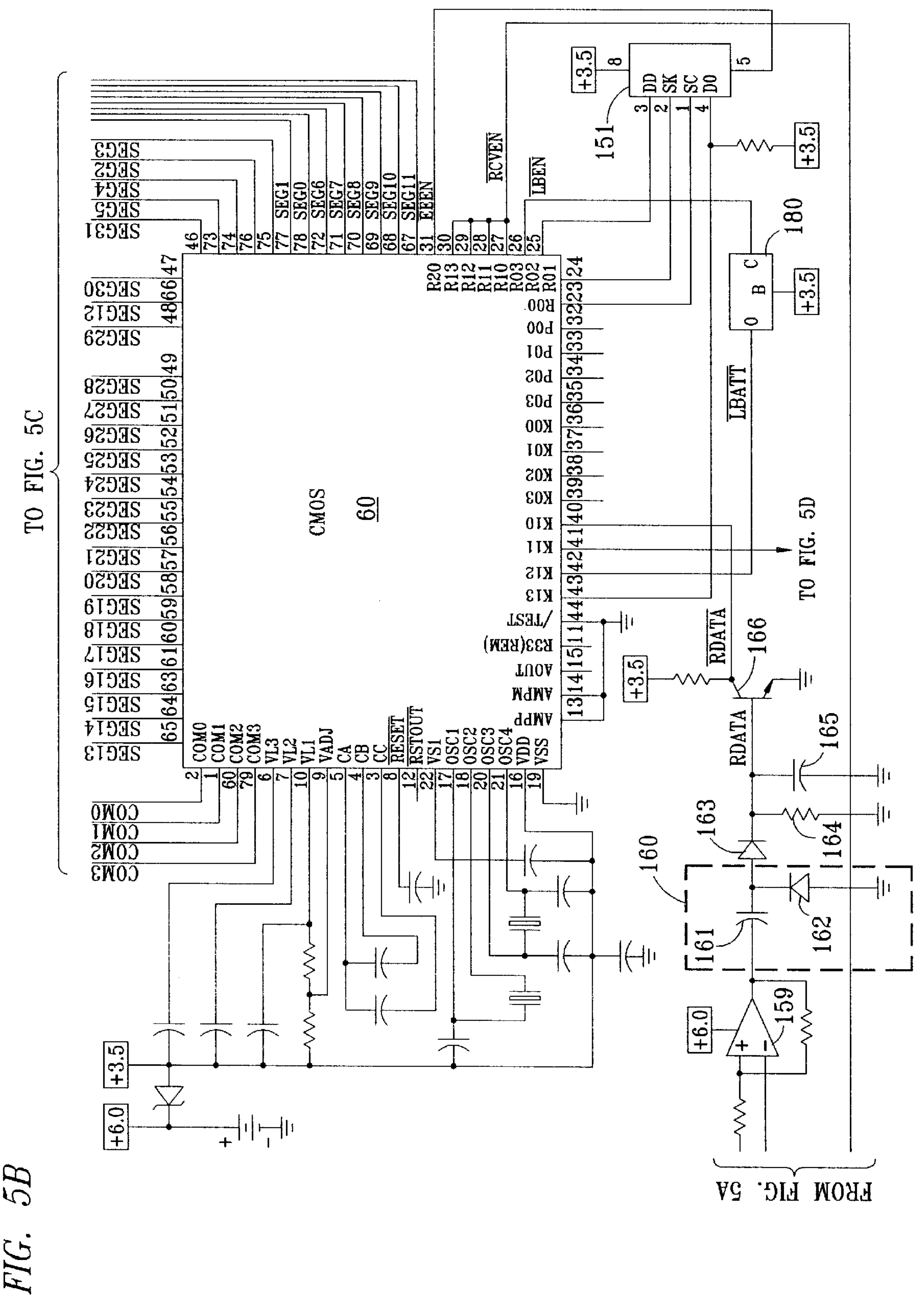
Figure 5C:
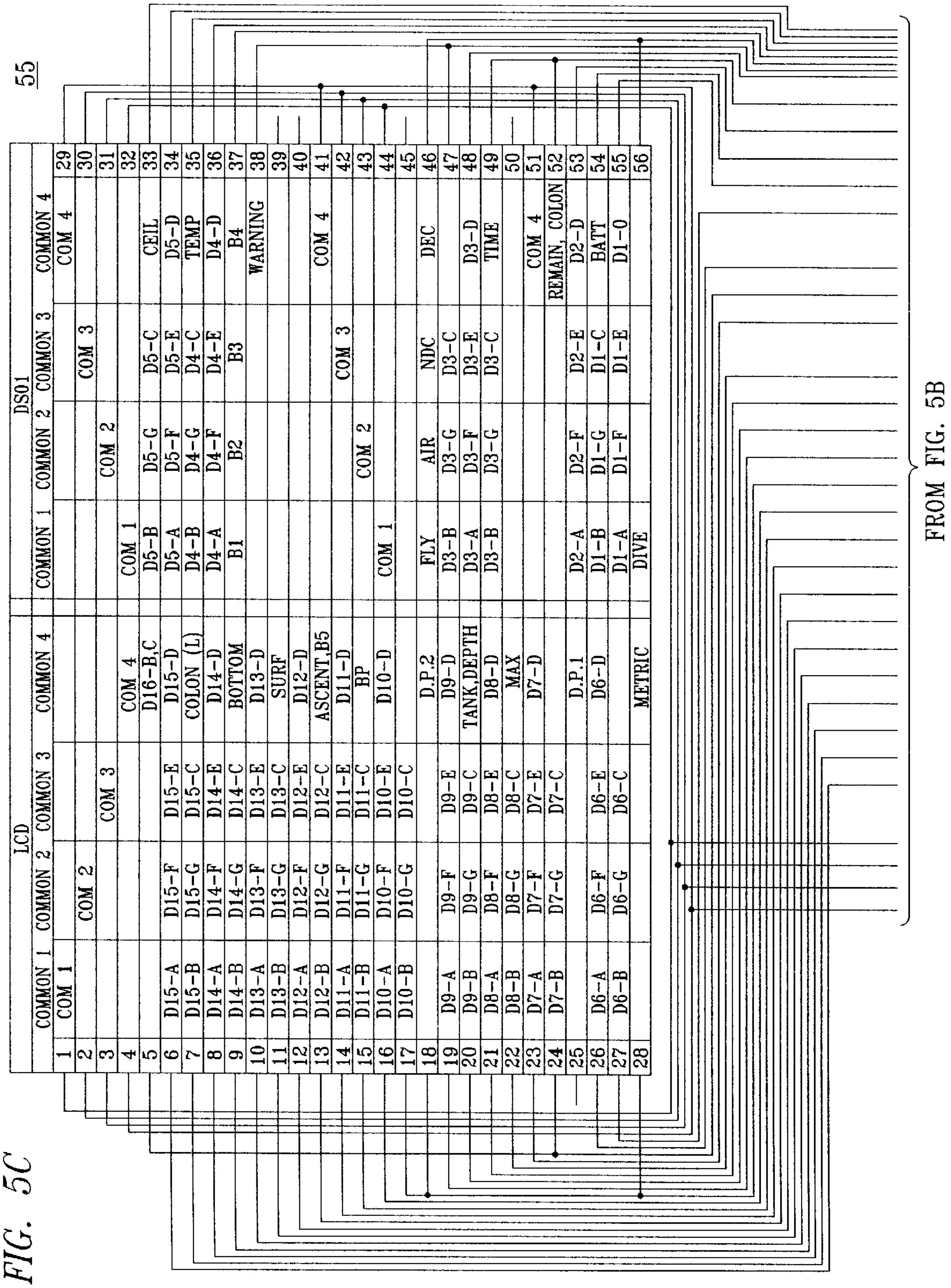
Figure 5D:
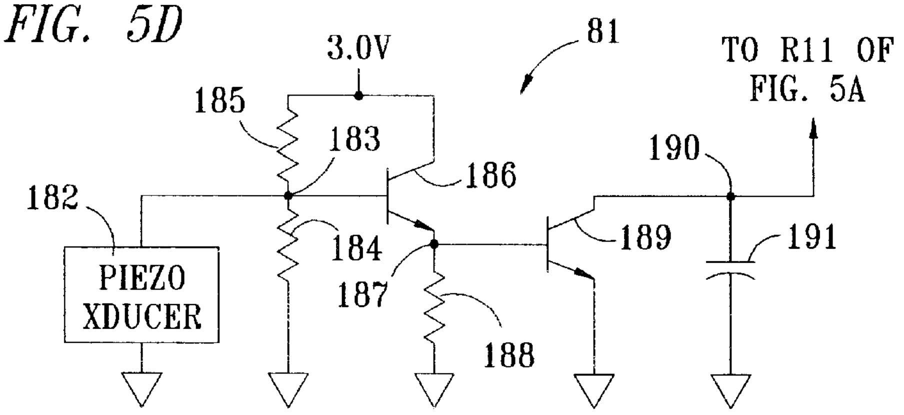

Referring now to FIG. 5D, there is illustrated a schematic diagram of a wrist activated device provided by the tap-on device 81 in the display unit. The tap-on device 81 comprises a piezoelectric transducer 182, which is connected between a node 183 and ground. Node 183 is connected with the center of a resistive divider, comprised of a first resistor 184 connected between node 183 and ground and a second resistor 185 connected between node 183 and a voltage of 3.0 volts. Node 183 is also connected to the base of an NPN transistor 186, the collector thereof connected to the 3.0 volt node and the emitter thereof connected to a node 187. A resistor 188 is connected between node 187 and ground. Node 187 also drives the base of an NPN transistor 189, the emitter thereof connected to ground and the collector thereof connected to a node 190. Node 190 is connected to one plate of an integrating capacitor 191, the other plate thereof connected to ground. The capacitor 191 has a value of 0.47 microfarads.

In operation, the piezoelectric transducer 182 is operable to generate a small voltage when stressed. This voltage will be applied to node 183 which will in turn apply sufficient current to the node 187 to turn on transistor 189. When transistor 189 is turned on, it will effectively short the plate of capacitor 191 to ground. When this occurs, the signal to the pin K11 of the processor 60 will be effectively shorted. This short will be recognized by the system.

Capacitor 191 may be effectively shorted to ground as described above by a single voltage pulse produced by the piezoelectric device 182. A shorted condition of capacitor 191 is required for a pre-determined time period to activate the system. As will be described hereinbelow, the pulses are derived from either tapping the display case or from sharply rotating the wrist.

Figure 5E:
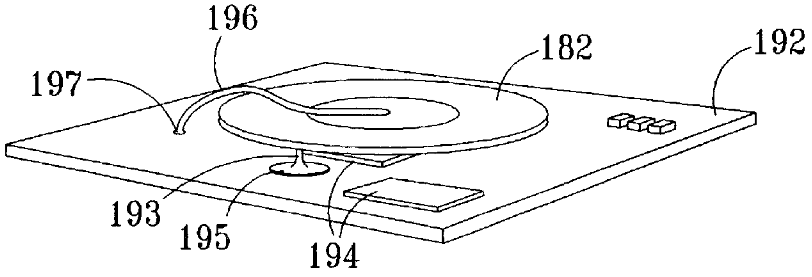
FIG. 5E is a perspective view of the transducer and the mounting thereof.

Referring now to FIG. 5E, there is illustrated a perspective view of a PC board 192, such that a wrist activated device is provided by tap-on device 80 with the piezoelectric device 182 disposed in a cantilever fashion above the surface of the PC board 192. The piezoelectric device 182 is a disc shaped device that is supported by a pedestal 193 on one edge thereof, such that it extends out over the PC board 192 and within the boundaries thereof. There are a number of integrated circuits 194 disposed on the surface, these being such things as the microprocessor 60 and various buffered gates. The pedestal 193 is connected to an electric contact 195 on the surface of the substrate 192 to allow it to be connected to, for example, the ground terminal. The center of the piezoelectric device 182 is connected via a wire 196 from the top thereof to an electrical connection 197 on the PC board 192. By providing the cantilever configuration with only a pedestal on one edge of the disc shaped piezoelectric transducer 182, any tapping of the housing to which the substrate 192 is mounted or sudden movement thereof will cause a flexing of the piezoelectric transducer 182 about the pedestal 193. This flexing will, of course, cause the piezoelectric transducer 182 to output a signal. Since the piezoelectric transducer has a certain mass associated therewith, any sudden movements either vertically or rotationally about the pedestal will cause a flexing. This will not be as noticeable with a rotation or movement in the plane of PC board 192, but vertical movement or rotational movement will more readily cause such an output.

Figure 5F:
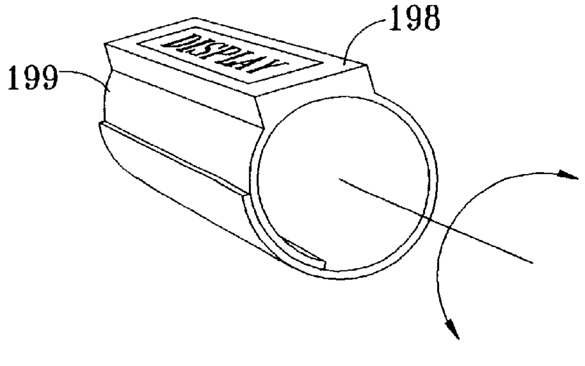
FIG. 5F is a perspective view of the display device housing.

Referring now to FIG. 5*f*, there is illustrated a diagrammatic view of a housing 198 which is attached to a wrist member 199 for attachment to the wrist of the user. The housing 198 will house the display and the PC board 192. With such a configuration, the user need only to rotate their wrist to create sufficient stress on the piezoelectric transducer 182 in order to generate a signal. This is to be compared with the above described technique of attaching the piezoelectric transducer to the inside of a case, this being the tank unit. In this configuration, localized tapping must be required. With the configuration illustrated in FIG. 5*e*, any inertia imparted to the housing will cause the signal to be generated. Of course, the processor is adjusted such that more than a single tap or a single shake of the wrist is required to indicate a valid signal for system activation. There must be a number of sequential signals in order to increment a counter. This, of course, is a software counter which is part of the instruction code of the processor. In general, it merely examines the input pin K11 and, when it sees the pin go low, it registers this as a count value. If it does not see another transition in a predetermined duration of time, the count value is reset to zero.

Figures 7A, 7B:
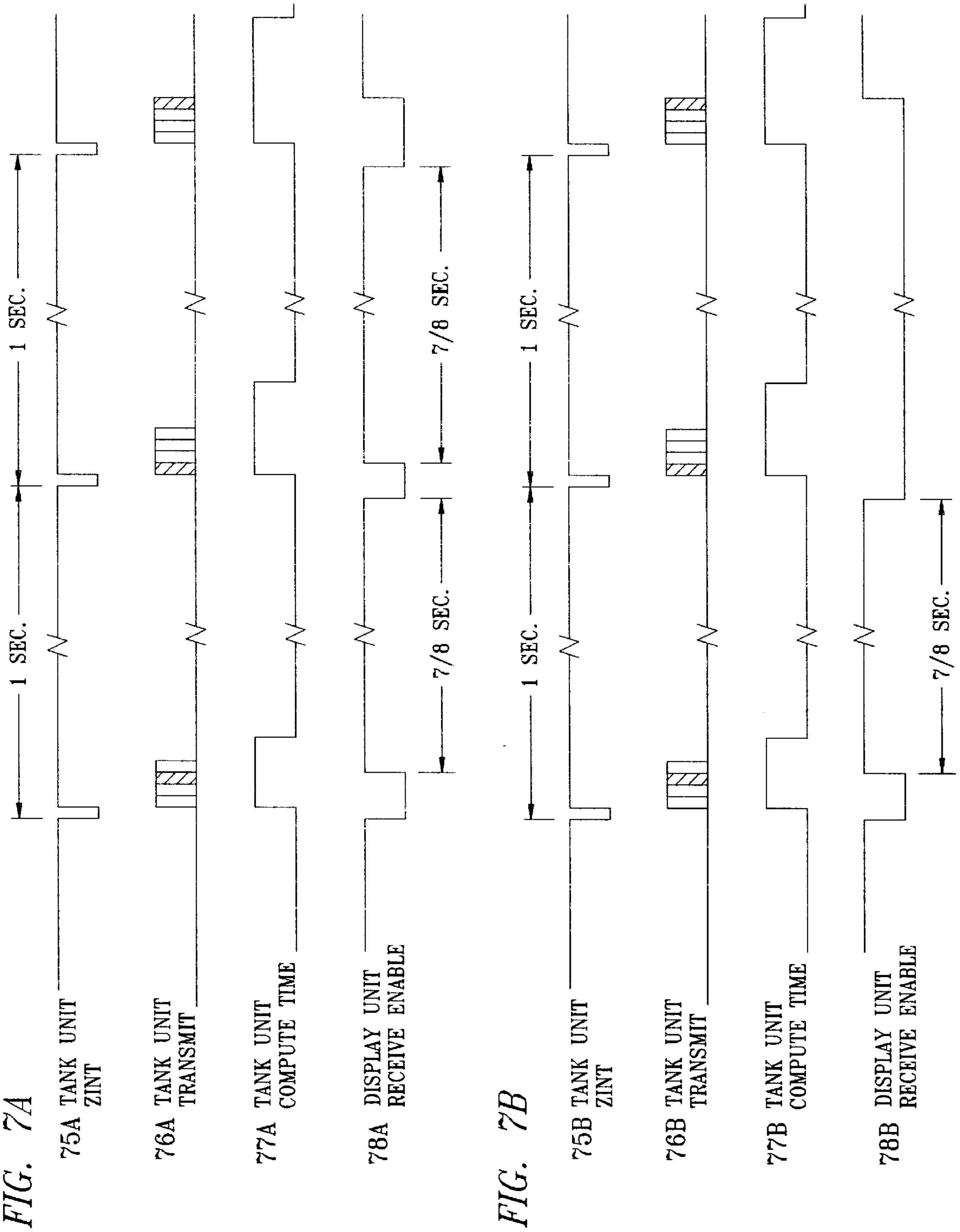
FIGS. 7A and 7B are timing diagrams which illustrate the relationship between the transmission of data by the tank unit and reception of data by the display unit of the dive computer.

FIGS. 7A through 7B are timing diagrams that illustrate the relationship between data transmitted by the tank unit and data received by the display unit. FIG. 7*a* shows transmissions between the tank unit and display unit without error. Time line 75*a* illustrates the tank unit ZINT_bar signal, which occurs once every second. Time line 76*a* illustrates the tank unit transmit period. As noted above, when microprocessor 36 receives the ZINT_bar signal, it transmits the user's dive parameters from the previous "awake" period and calculates and stores the user's current dive parameters. Once every second, the ZINT_bar signal causes the tank unit 20 to transmit data in one of four possible time slots. The tank unit randomly chooses the time slot in which to transmit data. The cross-hatched area on time line 76*a* illustrates the tank unit sending data during the third, first, and fourth time intervals of the tank unit transmit period. Time line 77*a* illustrates the tank unit compute period. After microprocessor 36 is "awakened" by the ZINT_bar signal, it immediately begins computing the user's current dive parameters. When it has transmitted the data from the previous "awake" period and computed and stored the user's current dive parameters, microprocessor 36 "goes back to sleep." As shown by time line 77*a,* although the tank unit transmit period is a set non-varying interval, the tank unit compute time varies according to the complexity of the computation required. Time line 78*a* illustrates the function of the display unit receive enable (RCVEN_bar) signal, which enables the display unit receiver circuit 50 seven-eighths (⅞) of a second after reception of the previous data transmission and disables the display unit receiver circuit 50 immediately after it receives the current data transmission. As shown by time line 78*a,* the time interval during which the receiver circuit 50 is enabled varies due to the random nature of the tank unit transmit period. Limiting the time period during which the display unit will accept data transmissions from the tank unit reduces the likelihood of the display unit receiving data for another user's tank unit.

FIG. 7*b* illustrates that ability of the display unit to recover from a missed reception. Time lines 75*b* through 77*b* are the same as time lines 75*a* through 77*a.* As shown by time line 78*b,* however, if the display unit does not receive a data transmission, in this case the second data packet, the receive enable signal continues to hold the display unit receiver circuit 50 open until the display un it receives the next data transmission, in this case, the third data packet. After the display unit receives a data transmission, it immediately disables the display unit receiver circuit 50 and then enables the display unit receiver circuit 50 seven-eighths (⅞) of a second later. The display unit then continues to operate as illustrated by FIG. 7*a.* (In the preferred form, if the display unit fails to receive a data transmission for five seconds, it flashes the last data received from the tank unit.)

The Display 55

Returning to FIG. 5, microcomputer 60 is directly connected to a liquid crystal display 55 by four common lines and thirty-two (32) segment driver lines. In the preferred form, liquid crystal display 55 is a twisted noematic-type display with dark segments on a clear background and has a reflective-type polarizer on the back of the display. Microcomputer 60 generates varying amplitude, times synchronized signal on the four common and thirty-two (32) segment lines to address the segments to be either "on" or "off."

Figure 8A:
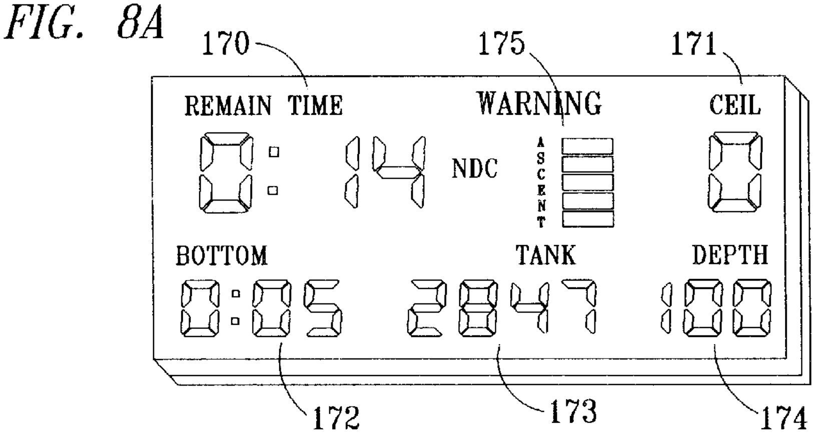
FIGS. 8*a* and 8*b* illustrates typical dive parameter information displayed on a normal screen and an alternate screen as controlled by the user of the display unit.
Figure 8B:
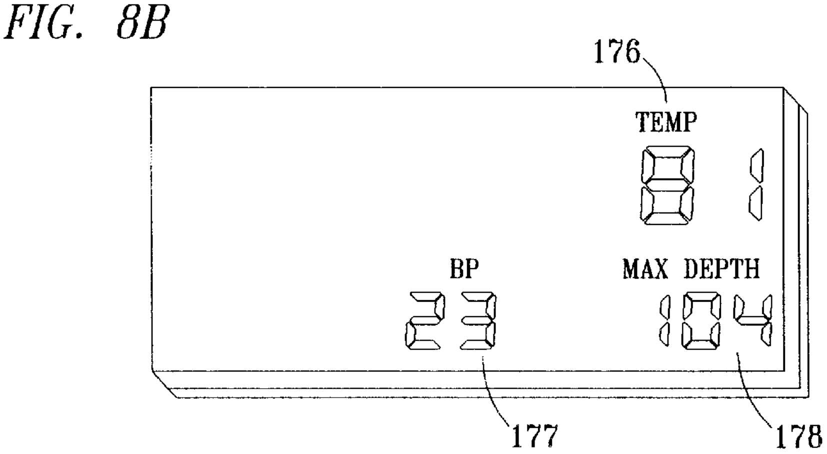

In the preferred form, the information displayed by the display unit can be switched between a normal screen and an alternate screen. FIGS. 8*a* and 8*b* illustrate the information capable of being displayed on the dive computer display unit 25. FIG. 8*a* illustrates the normal screen of display unit 25 when the dive computer is submerged. In this mode, the display unit 25 displays air-time remaining 170, ceiling 171, bottom time 172, tank pressure 173, depth 174, and an ascent rate bar graph 175.

Air-time remaining 170 is a prediction of the time it will take the user to use the air remaining in compressed-air tank 13 at the user's current breathing rate.

Ceiling 171 is the depth to which the user may ascend before completing a decompression stop. In the preferred form, ceiling depths are given in 10-foot increments from 0 to 30 feet. When programmed to display depth in meters, ceiling depths are shown in increments of 3 meters from 0 to 9 meters. When the user is making a "no compression" dive, the ceiling 171 will read 0, indicating that the user may safely make a direct ascent to the surface without completing any decompression stop. Bottom time 172 begins to count when the user has descended below 5 feet in the preferred form, and continues to be counted until the user has ascended above 3 feet.

Tank pressure 173 is the air pressure in compressed-air tank 13. In the preferred form, tank pressure is displayed in increments of 1 psi (or 0.1 bar or 0.1 kg/cm$^2$ in metric units). In the preferred form, if the air pressure drops below 500 psi or below 5 minutes of air-time remaining, the dive computer sounds an audible warning, displays a warning legend on the display unit, and causes the warning legend and tank pressure 173 digits to flash.

Depth 174 is the depth of the user. As noted above, when the tank unit is submerged, it automatically calibrates its depth measurement for either fresh water or sea water and computes the user's actual depth based on the measured ambient pressure. In the preferred form, the range displayed is from 0 to 250 feet in increments of 1 foot. When depth is displayed in meters, its range is from 0 to 76 meters in increments of 1 meter.

The ascent rate bar graph 175 allows the user to monitor the rate of ascent. In the preferred form, each bar represents an ascent rate of an additional 10 feet per minute with a maximum ascent rate of 60 feet per minute allowed. For example, an ascent rate of 35 feet per minute will cause the ascent bar graph 175 to display three bars, while an ascent rate of 60 feet per minute will cause the ascent bar graph 175 to display all five bars. An ascent rate slower than 10 feet per minute will not cause the ascent bar graph 175 to be illuminated.

FIG. 8*b* illustrates the alternate screen of display unit 25 when the dive computer is submerged. In this mode, the display unit 25 displays temperature 176, breathing parameter 177, and maximum depth 178. Temperature 176 is the ambient temperature of the water. Breathing parameter 177 is the indicator of the user's breathing efficiency discussed in detail above. And maximum depth 178 is the maximum depth that the user has descended to on that dive. In the preferred form, each dive parameter is updated once every second.

In the preferred form, the user can switch from the normal screen to the alternate screen by activating the wrist activated tap-on device 81 on the display unit 25. In this mode, only the presence of a single pulse from piezoelectric transducer 182 is required to switch to the alternate screen. Information on the alternate screen is displayed on LCD 55 for a short period of time before the display automatically switches back to the normal screen.

The display also includes a warning indicator to alert the user whenever certain dive parameters reach dangerous levels. For example, if the air pressure in the user's compressed-air tank drops below 500 psi, the display will cause a WARNING legend and the air pressure indicator to flash. This warning will continue until the tank unit is attached to a compressed-air tank with mor than 600 psi or the user surfaces. Similarly, if the user's breathing parameter goes to either zero or 99, the display will cause the WARNING legend and the diver's breathing parameter to flash and continue flashing until the diver's breathing parameter returns to acceptable levels.

Low Battery Detect Circuit 180

The display unit also includes a low battery detect device 180 to warn the diver whenever the batteries in the display unit are below a certain voltage. In the preferred form, low battery detect circuit 180 consists of a SCI17701Y available from S-MOS, which transmits a signal to microcomputer 60.

The Display Unit Tap-On Switch 81

The display unit includes the wrist activated switch 81 for turning the display unit on and off, both of which eliminate the need for a sealed penetration of the case. The details of this are described hereinabove with respect to FIGS. 5E and 5F. Once the display unit determines that it has been turned on, the LCD 55 is initialized and the display unit begins displaying dive parameter data as it receives it from the tank unit, this being a primary display mode.

Figure 9:
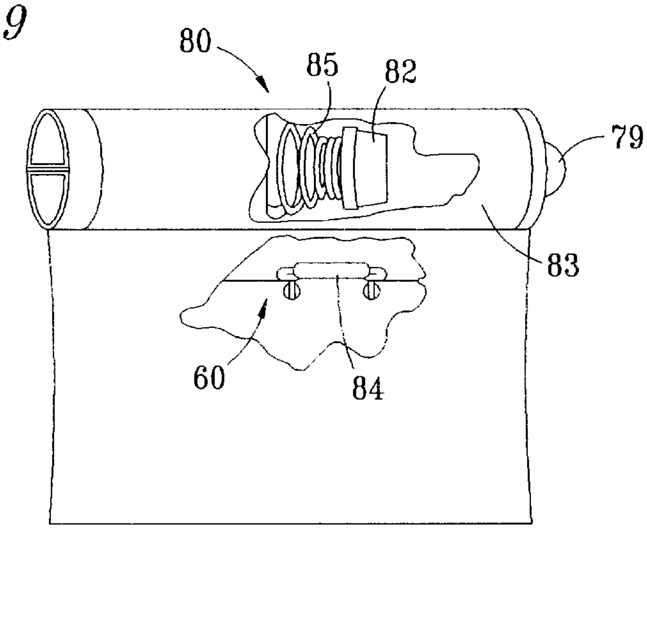
FIG. 9 is a diagram of the on/off switch used to turn the display unit of the dive computer on and off.

The display unit may, alternatively, include a push-button magnetic on-off switch 80, which is shown in FIG. 9. Push-button 79 is positioned so that when it is depressed, it causes ceramic magnet 82 to move along cylinder 83 until it is close enough to reed-switch 84 that the static magnetic field of the magnet activates reed-switch 84. Activation of reed-switch 84 is detected by microcomputer 60, which causes the display unit to initialize LCD 55 and begin displaying dive parameter data as it receives it from the tank unit. When the user releases push-button 79, spring 85 returns ceramic magnet 82 to its non-depressed position.

Detailed Description of Data Probe 150

FIG. 10 illustrates tank unit 20 connected to personal computer 200 through data probe 150. As noted above, the data probe 150 can be both mechanically and electrically attached to the tank unit by the same three metal clasps, 21 through 23, that are used to attach the tank unit to the user's low-pressure hose 24, and can be connected to personal computer 200 through a standard RS-232 port. Metals clasps 21 through 23 of tank unit 20 attach to metal rings 202 through 204 of data probe 150 and RS-232 connector 201 of data probe 150 attaches to the standard RS-232 port of personal computer 200. The active circuit elements of data probe 150 are physically contained in the data probe RS-232 connector 201.

FIG. 11 is an electrical schematic of the data probe 150 illustrated in FIG. 10. When the tank unit is attached to personal computer 200 through the data probe 150, control and data signals can be transmitted to the tank unit 20 through metal ring 202 and received from the tank unit through metal ring 204. Metal ring 203 is connected to ground. Metal rings 202 and 204 are connected to an RS-232 transceiver 205 through inverters 206 and 207. The principal function of RS-232 transceiver 205 is to convert data acceptable to the dive computer, which is between ground and +5 volts, to data acceptable to an RS-232 port of a personal computer, which is between −12 and +12 volts. In the preferred form, RS-232 transceiver 205 is a MAX231 available from Maxim.

The data probe RS-232 connector 201 is a twenty-five pin connector of which only five pins are used by the data probe. The data terminal ready (DTR) pin 208, receive data (RCV) pin 209, and ready to send (RTS) pin 211 are used to supply power to the active element of the data probe through three pairs of diodes 213, 214, and 215. These connections provide +12 volts and −12 volts to RS-232 transceiver 205 and +5 volts to RS-232 transceiver 205 and inverts 206 and 207 through +5 volt regulator 215, which converts +12 volts to +5 volts. In the preferred form, +5 volt regulator 913 is a 78L05 available from either TI or Motorola. Pin 212 is connected to ground.

In addition to providing power to the active elements of the data probe, the receive data pin 209 is also used to transmit serial data to the tank unit through RS-232 transceiver 205 and metal ring 202. The transmit data (XMIT) pin 210 is used to receive data from the tank unit through RS-232 transceiver 205 and metal ring 204.

In operation, the data probe 150 allows data and control signals to be exchanged between tank unit 20 and personal computer 200. This allows the user to recall dive profiles stored in the tank unit 20 and display those dive profiles on the personal computer. As noted above, the user can also read and modify EAROM 39 data to control the operational parameters of the dive computer.

Figure 12:
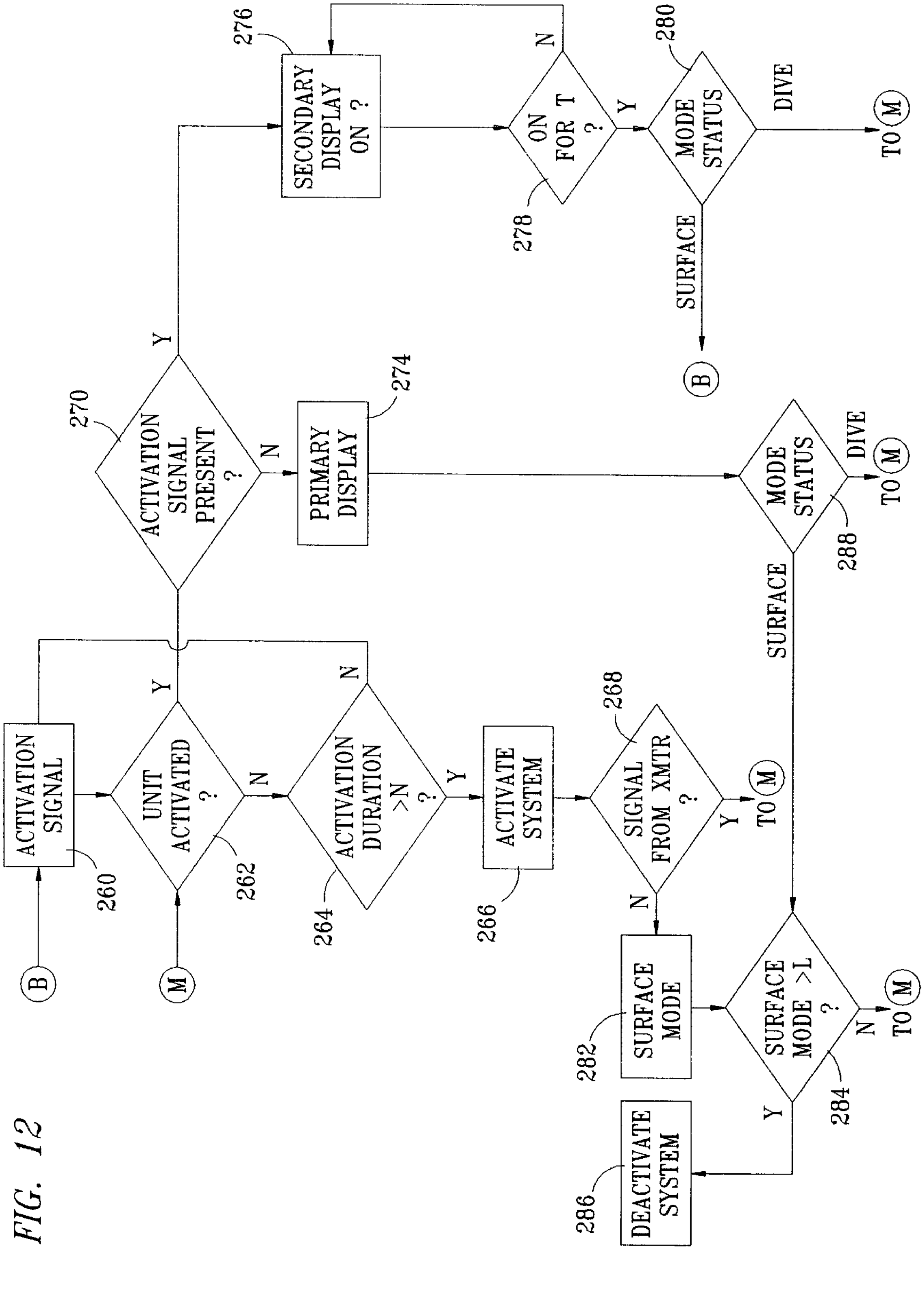
FIG. 12 is a flowchart of the operation of the display when switching between the alternate displays.

Referring now to FIG. 12, there is illustrated a flowchart depicting the operation of the "tap-on" device of the display unit. The program is initiated at a block 260 wherein the activation signal is generated. The deactivation signal is either the tapping of the housing or the rotation of the wrist which stresses the piezoelectric transducer in the display unit. The program then flows to a decision block 262 to determine if the display unit has been activated previously. If not, the program will flow to a decision block 264 to determine if the duration of the activation signal is greater than N. If not, the program will flow along an "N" path back to the block 260 until the activation signal has been present a sufficient duration of time. At this time, the program will flow from decision block 264 to a function block 266 to activate the system and then to a decision block 268 to determine if a signal has been received from the transmitter associated with the tank sending unit. If so, the program will flow back to the input to the decision block 262, indicated by the point M.

Once the system has been activated, the program will flow from the decision block 262, in response to receiving an activation signal that causes the program to flow to decision block 262, and then to a decision block 270 to determine if the activation signal is present. If an activation signal is not present, this indicates that the wrist is not being rotated or the individual is not tapping on the housing, this will cause the program to flow to the primary display block 274 and display the primary display function. However, if the unit had been previously activated and an activation signal was present, this indicates that the user is attempting to access an alternate display or access alternate functions. In the preferred embodiment, an alternate display is accessed and constitutes the alternate function, it being understood that other functions of the display device could be activated in this manner. The program will then flow along a "Y" path to a function block 276 to turn the secondary display on and then to a decision block 278 to determine if it has been on for a certain amount of time. The secondary display will stay on for only a certain period of time, prior to switching back to the primary display. The program will flow along an "N" path back to the block 276 and remain in this mode until the predetermined duration of time, at which time it will flow to a function block 280 to determine the mode status, i.e., whether it is a surface mode or a dive mode. This is determined by pressure sensors. If it is in the dive mode, the program will flow back to the input to decision block 262. If it is in the surface mode, the program will flow back to the block 260.

If, at the decision block 268, it was determined that the signal from the transmitter had not been received, but the system had been activated, the program will flow to a function block 282 to enter the surface mode and then to a decision block 284 to determine if the surface mode has been present for longer than a predetermined period of time. If not, it will flow back to decision block 262. However, if it has been in the surface mode for a sufficient amount of time, i.e., the individual has not entered the dive mode, the program will flow to a function block 286 to deactivate the system. This mode can be entered also from the primary display 274 which flows to a decision block 288 to determine the mode status and flows to decision block 284 if in the surface mode and to decision block 262 if in the dive mode.

Although the preferred embodiment has been described in detail, it should be understood that various changes, substitutions and alterations can be made therein without departing from the spirit and scope of the invention as defined by the appended claims.

What is claimed is:

1. A dive computer for use by a diver having an air tank, comprising:

sensors for measuring operating parameters of the air tank;

a tank processor for processing said sensed operating parameters of the tank in accordance with a predetermined processing algorithm to provide processed operating parameters, said tank processor having a transmitter for transmitting said processed operating parameters over a communication link;

a wrist processor for receiving from said communication link said processed operating parameters that were transmitted thereto by said tank processor, said wrist processor having:

a water tight housing, a transmit window in said housing, a display mounted in said housing adjacent to said window for viewing thereof through said window, a wrist processor section for receiving said transmitted processed operating parameters that are received from said communication link and processing the received processed operating parameters in accordance with a predetermined display processed algorithm to display information to the diver, a battery for powering said processor and said display, and an inertia switch for generating a control signal in response to external inertia forces imparted to said housing, said control signal controlling predetermined aspects of the operation, wherein the diver is allowed access to the operation of the processor without having to have access to an internal switch, which would effect the watertight nature of said watertight housing and said inertia forces can be imparted thereto without the use of both hands.

2. The dive computer of claim 1, wherein said operating parameters are breathing parameters.

3. The dive computer of claim 1, wherein said communication link is a wireless communication link.

4. The dive computer of claim 1, wherein said inertia switch is operable to generate said control signal and, in response to receiving said control signal, said processor section enters a sleep mode and turns said display off to minimize power drain from said battery.

5. The dive computer of claim 1, wherein said inertia forces are impacts imparted to said watertight housing by the diver.

6. The dive computer of claim 1, wherein said inertia forces are generated by sharp rotation of the diver's wrist upon which said wrist processor is disposed.

7. The dive computer of claim 6, wherein said inertia switch comprises a piezoelectric transducer which generates a signal in response to stress associated therewith, said stress derived from said inertial forces imparted to said housing by the diver and circuitry for receiving the signal from said piezoelectric transducer and generating an electrical control signal for input to said processor section, said processor section recognizing an electrical control signal.

8. The dive computer of claim 7, wherein said inertia forces imparted in the form of rotation to said piezoelectric transducers must be impulses which are counted by said processor section and, after a predetermined number of counts, said processor section declares said inertia forces present in sufficient number and frequency to constitute said control signal.

9. The dive computer of claim 7, wherein said piezoelectric transducer comprises a disc shaped piezoelectric transducer having first and second electrical contacts and mounted onto a substrate with a pedestal, said pedestal disposed proximate the edge of said piezoelectric transducer on one side thereof and extending from the surface of said substrate, such that any inertial forces imparted to said watertight housing will be imparted to said substrate and said piezoelectric transducer will experience rotational forces about the proximal end of said pedestal, with said first and second electrical contacts connected to said processor section to generate a signal that is amplified and input to said processor section.

10. The dive computer of claim 1, wherein the processor section is operable to process said received processed operating parameters in accordance with first and second display process algorithms to generate first and second display information, said processor section controlling said display to display either said first or second display information at any given time, wherein said control signals from said inertia switch are operable to signal to said processor section the operation wherein said display information displayed on said display is alternated between said first and second display information, wherein the diver is allowed, through generation of said external inertial forces, to switch said display between said first and second display information.

11. A dive computer for use by a diver having an air tank, comprising:

a sensor for measuring an operating parameter;

a processor for processing said sensed operating parameter in accordance with a predetermined processing algorithm to provide a processed operating parameter;

a display for displaying said processed operating parameter;

a battery for providing operating power to at least one of said display and said processor;

a water tight housing; and an inertia switch disposed in said water tight housing for generating a control signal in response to external inertia forces imparted to said water tight housing, said control signal controlling predetermined aspects of operation of said dive computer, wherein the diver is allowed access to the operation of the processor without having to have access to an internal switch, which would effect the water tight nature of said water tight housing.

12. The dive computer of claim 11, wherein said processed operating parameter comprises a breathing parameter of the diver.

13. The dive computer of claim 11, wherein said processor is disposed in a processor housing which is distally spaced from said water tight housing, and a wireless communication link interfaces between said inertia switch and said processor.

14. The dive computer of claim 11, wherein said inertia switch is operable to generate said control signal and, in response to receiving said control signal, said processor enters a sleep mode and turns said display off to minimize power drain from said battery.

15. The dive computer of claim 11, wherein said inertia forces are impacts imparted to said watertight housing by the diver.

16. The dive computer of claim 11, wherein said water tight housing is mounted to a wrist of the diver, and said inertia forces are generated by sharp rotation of the diver's wrist.

17. The dive computer of claim 16, wherein said inertia switch comprises a piezoelectric transducer which generates a signal in response to stress associated therewith, said stress derived from said inertial forces imparted to said water tight housing by the diver and circuitry for receiving the signal from said piezoelectric transducer and generating an electrical control signal for input to said processor, said processor recognizing an electrical control signal.

18. The dive computer of claim 17, wherein said inertia forces imparted in the form of rotation to said piezoelectric transducers must be impulses which are counted by said processor and, after a predetermined number of counts, said processor declares said inertia forces present in sufficient number and frequency to constitute said control signal.

19. The dive computer of claim 17, wherein said piezoelectric transducer comprises a disc shaped piezoelectric transducer having first and second electrical contacts and mounted onto a substrate with a pedestal, said pedestal disposed proximate the edge of said piezoelectric transducer on one side thereof and extending from the surface of said substrate, such that any inertial forces imparted to said watertight housing will be imparted to said substrate and said piezoelectric transducer will experience rotational forces about the proximal end of said pedestal, with said first and second electrical contacts connected to said processor to generate a signal that is amplified and input to said processor.

20. The dive computer of claim 11, wherein said processor is operable to process said received processed operating parameters in accordance with first and second display process algorithms to generate first and second display information, said processor controlling said display to display either said first or second display information at any given time, wherein said control signals from said inertia switch are operable to signal to said processor the operation wherein said display information displayed on said display is alternated between said first and second display information, wherein the diver is allowed, through generation of said external inertial forces, to switch said display between said first and second display information.

* * * * *